US012620467B2

(12) United States Patent
Kakkesal et al.

(10) Patent No.:  US 12,620,467 B2
(45) Date of Patent:  May 5, 2026

(54) DATA EXTRACTION AND DATA-STRUCTURE TRANSFORMATION FOR IMPROVING DATA ACCESSIBILITY AND USAGE CONSISTENCY

(71) Applicant: Cerner Innovation, Inc., Kansas City, MO (US)

(72) Inventors: Aneesha Kakkesal, Karnataka (IN); Brianne Glasbrenner, Kansas City, MO (US); Narasimha Prasad, Karnataka (IN); Sayon Chakraborti, Karnataka (IN); Rohith Shetty, Karnataka (IN); Sandeepa Aithal, Karnataka (IN); Amit Mudugal Jagadeesh, Karnataka (IN); Disha Bundela, Karnataka (IN)

(73) Assignee: Cerner Innovation, Inc., Kansas City, MO (US)

( * ) Notice: Subject to any disclaimer, the term of this patent is extended or adjusted under 35 U.S.C. 154(b) by 170 days.

(21) Appl. No.: 18/666,060

(22) Filed: May 16, 2024

(65) Prior Publication Data

US 2025/0356975 A1    Nov. 20, 2025

(51) Int. Cl.
| | |
|---|---|
| *G06F 40/00* | (2020.01) |
| *G06F 40/186* | (2020.01) |
| *G06F 40/205* | (2020.01) |
| *G16H 20/10* | (2018.01) |

(52) U.S. Cl.
CPC ........... *G16H 20/10* (2018.01); *G06F 40/186* (2020.01); *G06F 40/205* (2020.01)

(58) Field of Classification Search
CPC ........ G16H 10/60; G16H 40/20; G06N 20/00; G06N 20/20; G06N 20/10; G06N 3/044;
(Continued)

(56) References Cited

U.S. PATENT DOCUMENTS 11,004,546 B2 *  5/2021  Freeburg, II ........... G16H 20/60
11,798,689 B2 * 10/2023  Hogue ................... G16H 20/40
(Continued)

OTHER PUBLICATIONS

Murray, Luke, et al. "Medknowts: unified documentation and information retrieval for electronic health records." The 34th Annual ACM Symposium on User Interface Software and Technology. 2021. (Year: 2021).*

*Primary Examiner* — Edgar X Guerra-Erazo
(74) *Attorney, Agent, or Firm* — Mughal Gaudry & Franklin PC

(57)    ABSTRACT

A system and computer-implemented method includes querying a data source for treatment plan templates based on a medical condition of a patient. Raw data related to treatment plan templates is received from the data source. The raw data includes text information. Raw data is parsed, and tags are identified. elements are extracted from the tags using complex regular expression and keywords. Formatted data is constructed from the elements in a machine-readable format. The elements are arranged in a hierarchical structure within the formatted data. Structured data having data frames is generated based on the formatted data. The structured data is provided to a medical provider for review. An update in the structured data is received from the medical provider based on a deviation in schedule provided in the treatment plan templates. The treatment plans are generated based on incorporation of the update into the structured data.

20 Claims, 13 Drawing Sheets

(58) Field of Classification Search

CPC ...... G06N 3/084; G06N 3/0442; G06N 3/045; G06N 3/0455; G06N 3/0464; G06N 3/047; G06N 3/0475; G06N 3/048; G06N 3/08; G06N 3/088; G06N 3/0895; G06N 3/09; G06N 3/091; G06N 3/092; G06N 3/094; G06N 3/096; G06N 5/00; G10L 25/30; G10L 2015/228; G06F 40/40

See application file for complete search history.

(56) References Cited

U.S. PATENT DOCUMENTS 12,131,811 B2 * 10/2024 Burch ..................... G10L 15/22

| | | | | |
|---|---|---|---|---|
| 2008/0000993 | A1* | 1/2008 | Jung ..................... | G16H 20/10 |
| | | | | 235/495 |
| 2008/0000994 | A1* | 1/2008 | Jung ..................... | G16H 50/20 |
| | | | | 235/495 |
| 2014/0122127 | A1* | 5/2014 | Smith ................... | G16H 40/63 |
| | | | | 705/3 |
| 2018/0102190 | A1* | 4/2018 | Hogue .................. | G16H 10/60 |
| 2019/0180876 | A1* | 6/2019 | Brown .................. | G16H 20/10 |
| 2020/0082932 | A1* | 3/2020 | Salinas ................ | G16H 80/00 |
| 2020/0152297 | A1* | 5/2020 | Freeburg, II .......... | G16H 20/60 |
| 2022/0130504 | A1* | 4/2022 | Burch .................. | G16H 40/67 |
| 2023/0298722 | A1* | 9/2023 | Kumar .................. | G16H 40/67 |
| | | | | 705/2 |
| 2024/0061835 | A1* | 2/2024 | Subramanian ........ | G06F 16/252 |
| 2024/0062863 | A1* | 2/2024 | Burch ................ | G10L 15/1822 |

* cited by examiner

Figure 3:
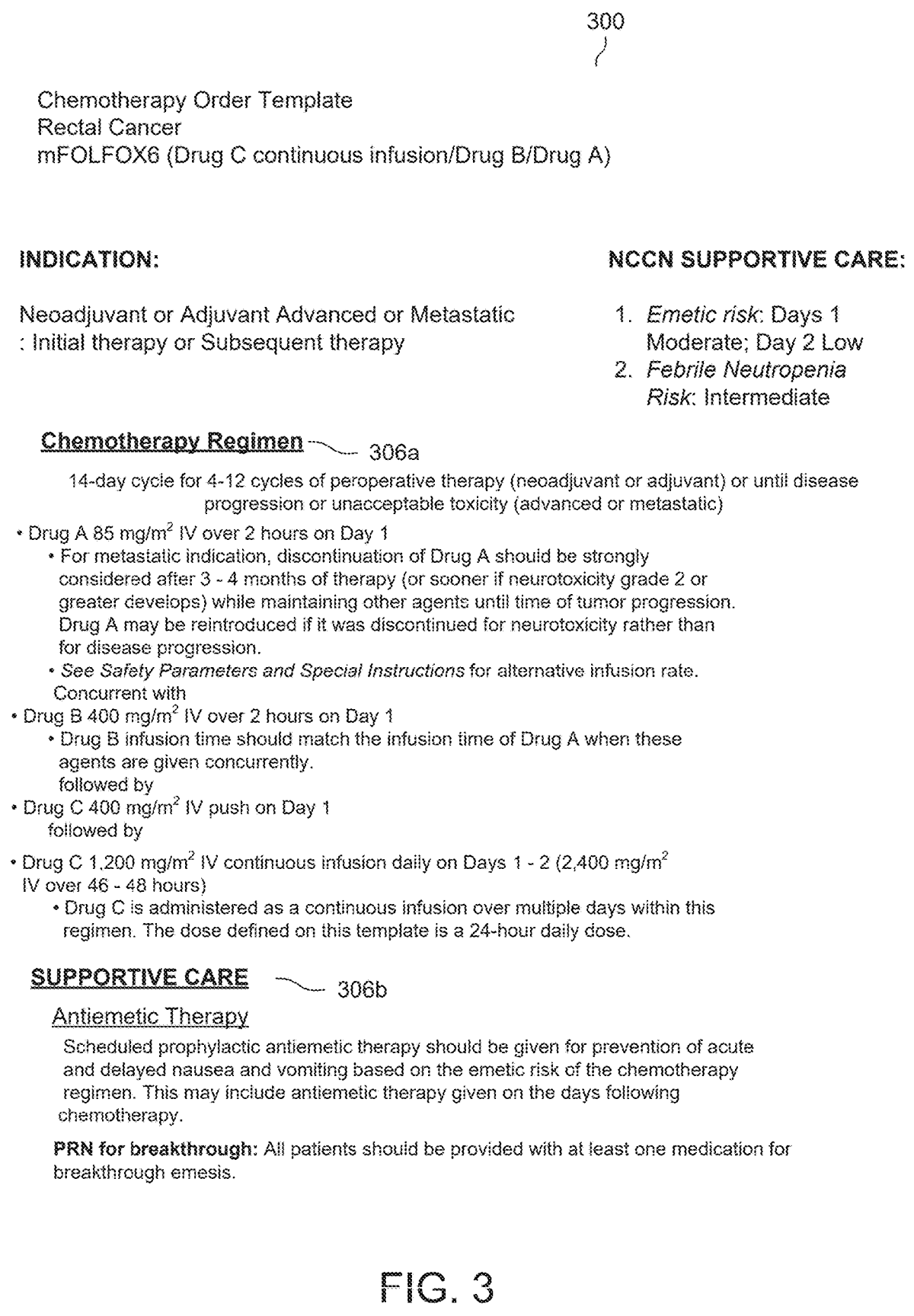

300

Chemotherapy Order Template
Rectal Cancer
mFOLFOX6 (Drug C continuous infusion/Drug B/Drug A)

INDICATION:

Neoadjuvant or Adjuvant Advanced or Metastatic
: Initial therapy or Subsequent therapy

NCCN SUPPORTIVE CARE:

1. *Emetic risk*: Days 1
   Moderate; Day 2 Low
2. *Febrile Neutropenia
   Risk*: Intermediate

Chemotherapy Regimen — 306a 14-day cycle for 4-12 cycles of peroperative therapy (neoadjuvant or adjuvant) or until disease progression or unacceptable toxicity (advanced or metastatic)

- Drug A 85 mg/m$^2$ IV over 2 hours on Day 1
  - For metastatic indication, discontinuation of Drug A should be strongly considered after 3 - 4 months of therapy (or sooner if neurotoxicity grade 2 or greater develops) while maintaining other agents until time of tumor progression. Drug A may be reintroduced if it was discontinued for neurotoxicity rather than for disease progression.
    - *See Safety Parameters and Special Instructions* for alternative infusion rate.
  Concurrent with
- Drug B 400 mg/m$^2$ IV over 2 hours on Day 1
  - Drug B infusion time should match the infusion time of Drug A when these agents are given concurrently.
  followed by
- Drug C 400 mg/m$^2$ IV push on Day 1
  followed by

- Drug C 1,200 mg/m$^2$ IV continuous infusion daily on Days 1 - 2 (2,400 mg/m$^2$ IV over 46 - 48 hours)
  - Drug C is administered as a continuous infusion over multiple days within this regimen. The dose defined on this template is a 24-hour daily dose.

SUPPORTIVE CARE — 306b

Antiemetic Therapy

Scheduled prophylactic antiemetic therapy should be given for prevention of acute and delayed nausea and vomiting based on the emetic risk of the chemotherapy regimen. This may include antiemetic therapy given on the days following chemotherapy.

PRN for breakthrough: All patients should be provided with at least one medication for breakthrough emesis.

| Chemotherapy Order Template Breast | ~ 402 |

NCCN SUPPORTIVE CARE:

INDICATION:

HER2 positive:
Recurrent unresectable
(local or regional) or
Metastatic - First-line 1. Emetic risk:
   Days 1, 8, and 15 Low
   (Option 1); Day 1 Low;
   Days 8 and 15 Minimal
   (Option 2, Trasutuzumab
   weekly)

2. *Febrile Neutropenia
   Risk*: Intermediate

| Chemotherapy Regimen | ~ 404 |

| 21-day cycle until disease progression or unacceptable toxicity | ~ 406 |

. Pertuzumab
　. 840 mg IV over 60 minutes on Day 1 of Cycle 1 followed by
　. 420 mg IV over 30 minutes on Day 1 beginning with Cycle 2
. Trastuzumab
　. 8 mg/kg IV over 90 minutes on Day 1 of Cycle 1 followed by
　. 6 mg/kg IV over 30 minutes on Day 1 beginning with Cycle 2
　. Trastuzumab and hyaluronidase-oysk for subcutaneous injection may
　　be substituted for intravenous trastuzumab. Please see order
　　template <u>BRS 158</u> for trastuzumab and hyaluronidase-oysk dosing.
　. A biosimilar agent may be substituted if clinically appropriate.
　　Additional information on the use of biosimilars may be found
　　in <u>Appendix H : Biosimilars</u> and in disease-specific guidelines.

～408a or

. Trastuzumab
　. 4 mg/kg IV over 90 minutes on Day 1 of Cycle 1 followed by
　. 2 mg/kg IV over 30 minutes on Days 8 and 15 of Cycle 1 followed by
　. 2 mg/kg IV over 30 minutes on Days 1, 8, and 15 beginning with
　　Cycle 2

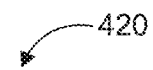

▽ <KNOWLEDGEPLAN>
    <NEWFORMAT>1</NEWFORMAT>
    <SOURCEORDERSETTYPE>MULTIPLAN</SOURCEORDERSETTYPE>
    <CAPTION>Pertuzumab + Trastuzumab + PACLitaxel</CAPTION>
    <PWCATID/>
    <UUID/>
    <DISPLAY/>
    <CKI/>
    <VERSION>1</VERSION>
    <TYPEMEAN>PATHWAY</TYPEMEAN>
    <EVIDENCEURL>URL:https://www.nccn.org/professionals/OrderTemplates/
      CottTemlateManagement/GetTemplateById/BRS88</EVIDENCEURL>
    <EVIDENCEURLTYPEMEAN>URL</EVIDENCEURLTYPEMEAN>
    <DISPLAYMETHODMEAN>SEQJENCED</DISPLAYMETHODMEAN>
    <PATHWAYTYPEDISP>Oncology</PATHWAYTYPEDISP>
    <CROSSENCOUNTERIND>1</CROSSENCOUNTERIND>
    <DIAGNOSISCAPTUREIND>/1</DIAGNOSISCAPTUREIND>
    <HIDEFLEXEDCOMPIND>0</HIDEFLEXEDCOMPIND>
    <CYCLEIND>1</CYCLEIND>
    <STANDARDCYCLENBR>99</STANDARDCYCLENBR>
    <DEFAULTVIEWMEAN/>
    <PROVIDERPROMPTIND>1</PROVIDERPROMPTIND>
    <ALLOWCOPYFORWARDIND>1</ALLOWCOPYFORWARDIND>
    <PATHWAYCLASSMEAN>ONCOLOGY</PATHWAYCLASSMEAN>
    <PROMPTONSELECTIONIND>1</PROMPTONSELECTIONIND>
    <DEFAULTVISITTYPEFLAG>3</DEFAULTVISITTYPEFLAG>
    <CYCLEBEGINNBR>0</CYCLEBEGINNBR>
    <CYCLEENDNBR>0</CYCLEENDNBR>
    <CYCLELABELDISP>Cycle</CYCLELABELDISP>
    <CYCLELOCKENDIND>0</CYCLELOCKENDIND>
    <CYCLEDISPLAYENDIND>0</CYCLEDISPLAYENDIND>

FIG. 4B

430 id="export-disease-title">Breast Cancer</span><span style="display: block; width: 100%; font-size: 19px; font-weight : bold; margin-bottom: 5px; word-wrap: break-word" id="export-regimen-title">Pertuzumab + Trastuzumab + PACLitaxel</span><div style="height: 5px; display: block; clear: both"></div></div></td><td style="vertical-align: top; height : 100%; "><span style="text-align: right ; display: block; width: 100%; vertical-align: top; float: right " id="export-template-id"><b>BRS88</b></span></td></tr></table></div><table id="export-template-info-section"><tr><td id="export-template-indication"><h4>INDICATION:</h4><span>HER2 positive: Recurrent unresectable (local or regional) or Metastatic - First-line</span></td><td id="export-template-references"><h4>REFERENCES:</h4><ol><li ><a href="http://www.nccn.org/professionals/physician_gls/PDF/breast .pdf">NCCN Guidelines<sup>®</sup></sup> for Breast Cancer V.4.2023.</a></li><li><a href="http://cancerres.aacrjournals.org/ content/72/24_Supplement/P5-18-20">Datko F, et al. <em>Cancer Res</em>. 2012;72(24 Suppl) :abstr P5-18-20.</a><sup><a href="https://www.nccn.org/professionals/OrderTemplates/PDF/appendix_E.pdf" title="The NCCN Guidelines include this article, and the template is consistent with this article." >a</a></a></sup></li><li><a href="http://www.ncbi.nlm.nih.gov/pubmed/14507946">Leyland-Jones B , et al. <em>J Clin Oncol</em>. 2003; 21 (21) : 3965-71 </a><sup><a href="https://www.nccn.org/professionals/OrderTemplates/PDF/appendix_E.pdf" title="The NCCN Guidelines include this article, and the template is consistent with this article.">a</a></a></sup></li></ol></td><td id="export-template-emetic-risks"><h4>NCCN SUPPORTIVE CARE:</h4><ol><li><i>Emetic risk:</i></div style="display: inline-block">NBSPDays 1, 8, and 15 Low (Option 1); Day 1 Low; Days 8 and 15 Minimal (Option 2, Trasutuzumab weekly)</div></li><li><i>Febrile Neutropenia Risk:</i><span>NBSPIntermediate</span></li></ol></td></tr></table></div><div style="clear: both;" >< /div><div id="export-template-regimens"><div><h4><span>hemotherapy <span>R</span>egimen</h4><i>21-day cycle until disease progression or unacceptable`

| | TEMPLATE CODE | TEMPLATE TITLE | CAPTION AND DISPLAY UNDER KNOWLEDGE PLAN | REGIMEN ID | DEFINITION | RELATIONS | SELECTABLE |
|---|---|---|---|---|---|---|---|
| 1 | | | | | | | |
| 2 | BRS88 | Breast Cancer | Pertuzumab+Trastuzumab+PACLitaxel | regimenPart -304258 | 21-day cycle until disease progression or unacceptable toxicity | | AND |
| 3 | BRS88 | Breast Cancer | Pertuzumab+Trastuzumab+PACLitaxel | regimenPart -304259 | 21-day cycle until disease progression or unacceptable toxicity | | OR |

| TEMPLATE TITLE | CAPTION AND DISPLAY UNDER KNOWLEDGE PLAN | REGIMEN ID | SELECTABLE | GRP ID | RELATION | DRUG ID |
|---|---|---|---|---|---|---|
| Breast Cancer | Pertuzumab+Trastuzumab+PACLitaxel | regimenPart-304258 | | 1 | | 402531-1 |
| Breast Cancer | Pertuzumab+Trastuzumab+PACLitaxel | regimenPart-304258 | | 1 | after - Pertuzumab-402531 | 402532-1 |
| Breast Cancer | Pertuzumab+Trastuzumab+PACLitaxel | regimenPart-304258 | | 2 | | 402537-1 |
| Breast Cancer | Pertuzumab+Trastuzumab+PACLitaxel | regimenPart-304258 | | 2 | after - Trastuzumab-402537 | 402538-1 |
| Breast Cancer | Pertuzumab+Trastuzumab+PACLitaxel | regimenPart-304258 | OR | 3 | | 402533-1 |
| Breast Cancer | Pertuzumab+Trastuzumab+PACLitaxel | regimenPart-304258 | | 3 | after - Trastuzumab-402533 | 402534-1 |
| Breast Cancer | Pertuzumab+Trastuzumab+PACLitaxel | regimenPart-304258 | | 3 | after - Trastuzumab-402533 and after - Trastuzumab-402534 | 402535-1 |
| Breast Cancer | Pertuzumab+Trastuzumab+PACLitaxel | regimenPart-304258 | | 5 | | 402536-1 |
| Breast Cancer | Pertuzumab+Trastuzumab+PACLitaxel | regimenPart-304259 | | 1 | | 402539-1 |
| Breast Cancer | Pertuzumab+Trastuzumab+PACLitaxel | regimenPart-304259 | | 1 | after - Pertuzumab-402539 | 402540-1 |
| Breast Cancer | Pertuzumab+Trastuzumab+PACLitaxel | regimenPart-304259 | | 2 | | 402545-1 |
| Breast Cancer | Pertuzumab+Trastuzumab+PACLitaxel | regimenPart-304259 | | 2 | after - Trastuzumab-402545 | 402546-1 |
| Breast Cancer | Pertuzumab+Trastuzumab+PACLitaxel | regimenPart-304259 | OR | 3 | | 402541-1 |
| Breast Cancer | Pertuzumab+Trastuzumab+PACLitaxel | regimenPart-304259 | | 3 | after - Trastuzumab-402541 | 402542-1 |
| Breast Cancer | Pertuzumab+Trastuzumab+PACLitaxel | regimenPart-304259 | | 3 | after - Trastuzumab-402541 and after - Trastuzumab-402542 | 402543-1 |
| Breast Cancer | Pertuzumab+Trastuzumab+PACLitaxel | regimenPart-304259 | | 5 | | 402544-1 |

FIG. 5C

DATA EXTRACTION AND DATA-STRUCTURE TRANSFORMATION FOR IMPROVING DATA ACCESSIBILITY AND USAGE CONSISTENCY

FIELD

The present disclosure relates generally to select extraction and transformation of data embedded within files. More particularly, the present disclosure relates to systems and methods that detect select data content and that transforms the structure of the detected data to improve accessibility and usage consistency of the select data.

BACKGROUND

An oncology treatment plan is a comprehensive and individualized strategy designed by a team of healthcare professionals to guide the care of a cancer patient. It outlines the specific treatments, therapies, and interventions that will be used to manage the patient's cancer. This plan considers factors such as the type and stage of cancer, the patient's overall health, and their treatment goals. The importance of an oncology treatment plan cannot be overstated, as it serves as a roadmap for both the medical team and the patient, ensuring that the effective and appropriate treatments are administered, while also helping to manage side effects and monitor progress throughout the cancer journey. It plays an important role in improving the patient's chances of successful treatment and recovery.

Currently, the process of creating the oncology treatment plan involves a manual approach of gathering data from a data source and feeding relevant data into a health information system. For example, a user device receives an input from the analyst and translates the input into a query to the data source like National Comprehensive Cancer Network® (NCCN®) server. The data source provides templates associated with the treatment plan to the user device. The analyst may download the templates. The templates obtained from the data source may be present in different data formats, such as an Extensible Markup Language (XML) format, a Hypertext Markup Language (HTML) format, and a Portable Document Format (PDF) format. Further, the data obtained from the research institute includes a large quantity of data. After downloading, the analysts manually navigates through the large quantity of data to extract relevant data related to the treatment plan, such as medications, cycle definitions, dosing, frequency, routes of administration, premedication, and notes. Further, the analyst feeds the relevant data into the health information system to create a final treatment plan.

For extracting the relevant data, the analyst has to traverse through multiple flowcharts and large amount of data. Manual data entry and navigating through the large quantity of data is a tedious task and prone to errors.

BRIEF SUMMARY

In an embodiment, a computer-implemented method includes querying at least one data source for one or more treatment plan templates. At least one data source is queried based on the medical condition of a patient. Raw data related to one or more treatment plan templates is received from at least one data source in response to the querying. The raw data includes text information. Raw data is parsed, and one or more tags are identified. Elements required for preparing treatment plan are extracted from the one or more tags using complex regular expressions and a standard set of keywords.

Formatted data is constructed from the extracted elements in a machine-readable format. The elements are arranged in a hierarchical structure within the formatted data. Structured data having one or more data frames based on the formatted data is generated. Each data frame of the one or more data frames includes information related to a particular phase of a treatment schedule proposed in the one or more treatment plan templates. The structured data is provided to one or more devices associated with a medical provider for review in a natural language format. An update in the structured data is received from the one or more devices associated with the medical provider based on a deviation in existing schedule provided in the one or more treatment plan templates. The one or more treatment plans are generated based on incorporation of the update into the structured data. The one or more treatment plans are generated in at least one of the machine-readable format and the natural language format.

The formatted data is constructed using one or more headings present in the text information of the raw data. The formatted data is accessible by one or more applications pertaining to a health-care system. The raw data is received from at least one data source using an Application Programming Interface (API). The raw data is received in form of one or more of an Extensible Markup Language (XML) format, a Hypertext Markup Language (HTML) format, and a Portable Document Format (PDF) format. The machine-readable format is a Java Script Object Notation (JSON) format. The structured data is provided to the one or more devices associated with the medical provider in a spreadsheet format. One or more treatment plans are generated in XML format. The complex regular expression and the standard set of keywords are dynamically updated in real time. One or more tags include a Unique Identification Number (UIN) or Universal Unique Identifier (UUID) that are generated programmatically. The medical condition of the patient is determined based on information obtained from a patient information database. One or more errors in the structured data based on the review of the medical provider are identified and updated based on one or more errors. The one or more treatment plans based on the updated structured data is generated.

In another embodiment, a system comprising one or more processors, and a memory coupled to the one or more processors, the memory storing a plurality of instructions executable by the one or more processors, the plurality of instructions that when executed by the one or more processors cause the one or more processors to perform a set of operations. The set of operations include querying at least one data source for one or more treatment plan templates. At least one data source is queried based on the medical condition of a patient. Raw data related to one or more treatment plan templates is received from at least one data source in response to the querying. The raw data includes text information. Raw data is parsed, and one or more tags are identified. Elements required for preparing treatment plan are extracted from the one or more tags using complex regular expressions and a standard set of keywords. A formatted data is constructed from the extracted elements in a machine-readable format. The elements are arranged in a hierarchical structure within the formatted data. Structured data having one or more data frames based on the formatted data is generated. Each data frame of the one or more data frames includes information related to a particular phase of a treatment schedule proposed in the one or more treatment plan templates. The structured data is provided to one or more devices associated with a medical provider for review in a natural language format. An update in the structured data is received from the one or more devices associated with the medical provider based on a deviation in existing schedule provided in the one or more treatment plan templates. The one or more treatment plans are generated based on incorporation of the update into the structured data. The one or more treatment plans are generated in at least one of the machine-readable format and the natural language format.

The formatted data is constructed using one or more headings present in the text information of the raw data. The formatted data is accessible by one or more applications pertaining to a health-care system. The raw data is received from at least one data source using an Application Programming Interface (API). The raw data is received in form of one or more of an Extensible Markup Language (XML) format, a Hypertext Markup Language (HTML) format, and a Portable Document Format (PDF) format. The machine-readable format is a Java Script Object Notation (JSON) format. The structured data is provided to the one or more devices associated with the medical provider in a spreadsheet format. One or more treatment plans are generated in XML format. The complex regular expression and the standard set of keywords are dynamically updated in real time. One or more tags include a Unique Identification Number (UIN) or Universal Unique Identifier (UUID) that are generated programmatically. The medical condition of the patient is determined based on information obtained from a patient information database. One or more errors in the structured data based on the review of the medical provider are identified and updated based on one or more errors. The one or more treatment plans based on the updated structured data is generated.

In yet another embodiment, a non-transitory computer-readable medium storing a plurality of instructions executable by one or more processors that cause the one or more processors to perform operations. In one step, at least one data source is queried for one or more treatment plan templates. At least one data source is queried based on the medical condition of a patient. Raw data related to one or more treatment plan templates is received from at least one data source in response to the querying. The raw data includes text information. Raw data is parsed, and one or more tags are identified. Elements required for preparing treatment plan are extracted from the one or more tags using complex regular expression and a standard set of keywords. A formatted data is constructed from the extracted elements in a machine-readable format. The elements are arranged in a hierarchical structure within the formatted data. Structured data having one or more data frames based on the formatted data is generated. Each data frame of the one or more data frames includes information related to a particular phase of a treatment schedule proposed in the one or more treatment plan templates. The structured data is provided to one or more devices associated with a medical provider for review in a natural language format. An update in the structured data is received from the one or more devices associated with the medical provider based on a deviation in existing schedule provided in the one or more treatment plan templates. The one or more treatment plans are generated based on incorporation of the update into the structured data. The one or more treatment plans are generated in at least one of the machine-readable format and the natural language format.

The techniques described above and below may be implemented in a number of ways and in a number of contexts. Several example implementations and contexts are provided with reference to the following figures, as described below in more detail. However, the following implementations and contexts are but a few of many.

BRIEF DESCRIPTION OF THE DRAWINGS

Various embodiments are described hereinafter with reference to the figures. It should be noted that the figures are not drawn to scale and that the elements of similar structures or functions are represented by like reference numerals throughout the figures. It should also be noted that the figures are only intended to facilitate the description of the embodiments. They are not intended as an exhaustive description of the disclosure or as a limitation on the scope of the disclosure.

FIG. 3 illustrates an exemplary document illustrating raw data according to an embodiment of the present invention.

FIGS. 4A-4C illustrate another exemplary document illustrating raw data according to an embodiment of the present invention.

FIGS. 5A-5C illustrate a user interface according to an embodiment of the present invention.

DETAILED DESCRIPTION

Figure 1:
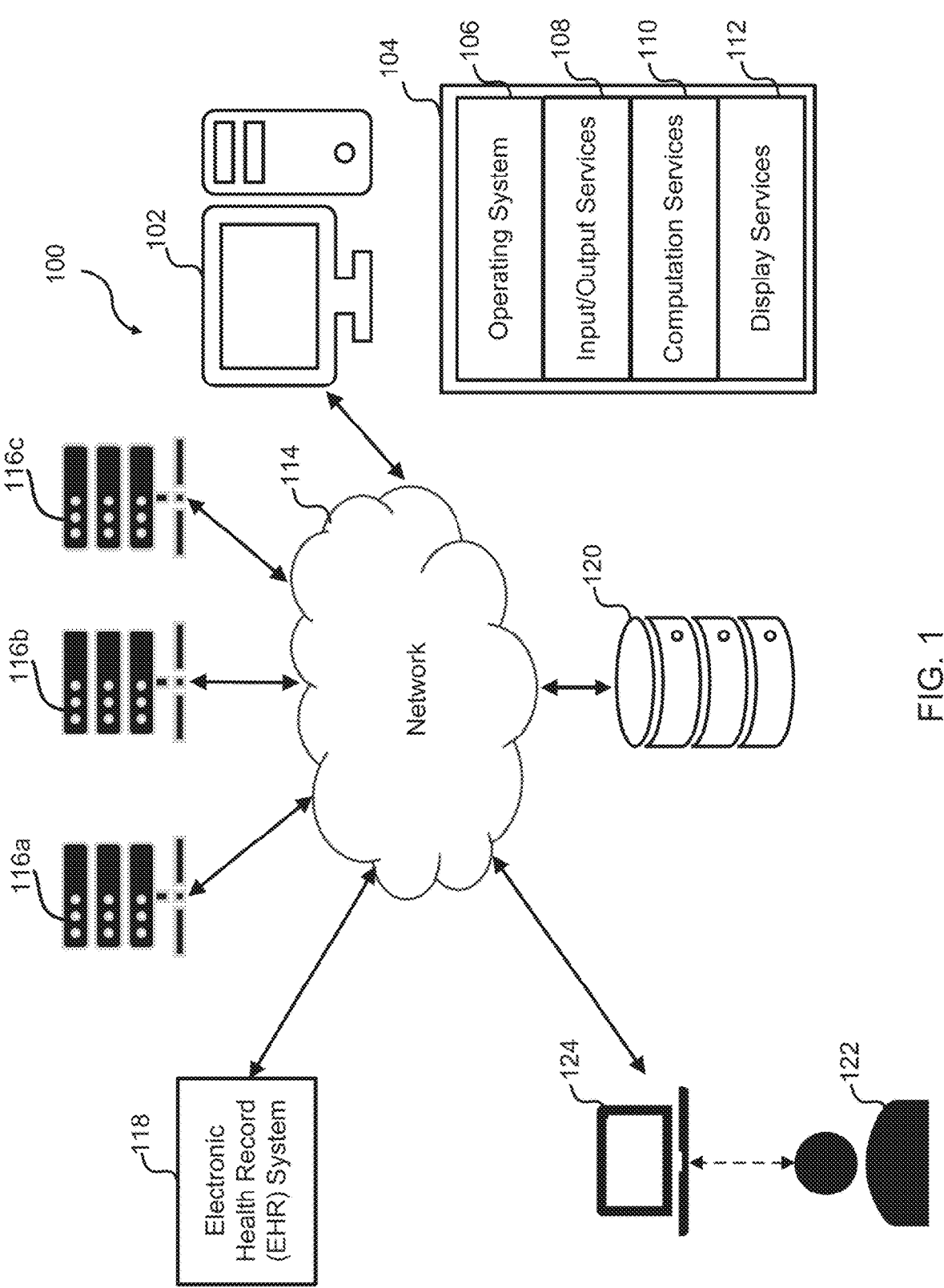
FIG. 1 illustrates example of a medical assistance system for constructing treatment plans for a patient according to an embodiment of the present invention.

In the following description, for the purposes of explanation, specific details are set forth in order to provide a thorough understanding of certain embodiments. However, it will be apparent that various embodiments may be practiced without these specific details. The figures and description are not intended to be restrictive. The word "exemplary" is used herein to mean "serving as an example, instance, or illustration." Any embodiment or design described herein as "exemplary" is not necessarily to be construed as preferred or advantageous over other embodiments or designs.

The term "healthcare data" is used to broadly refer to data resulting from, referenced in relation to, or characterizing interactions between a healthcare professional and another entity (e.g., a patient, another healthcare professional, a hospital, medical facility, or insurance company, etc.). The healthcare data may include a doctor's prescription, a lab report, a scan report, etc. The healthcare data may be obtained from patient healthcare records, billing records, laboratory orders and results, treatment plans and results, medication orders, an electronic health record (EHR), healthcare insurance information, medical or scientific literature, etc.

Certain aspects and features of the present disclosure relate to a technique for creating oncology treatment plans for a disease, such as cancer. For such purposes, a user device receives an input for obtaining treatment plan templates for a patient, such as a template code related to a medical condition of the patient. The medical condition of the patient may be determined using the healthcare data related to the patient. In an example, the user device may receive an input including a string "REC11" which indicates rectal cancer. The user device generates a query using the input received from the user and sends the query to a data source, such as a server of a research institute. For example, if the healthcare data related to the patient indicates a specific type of cancer, the data source may be queried for standard set of keywords may include standard terms that are generally utilized in a medical field.

The complex regular expression is used to create a Java Script Object Notation (JSON) object. The JSON object is utilized to create a template Excel file. The fetched template XML file has a series of XML and HTML tags that contain information about the medication, pre-medications and regimen. To fetch that information in the given order and format, regular expression is being used.

In an example, the regimen details are given in the template as follows between other XML tags.

```
<action id="regimenEntryGroup-290711-Example"><code><text value="regimen entry
group" /></code>
    <selectionBehavior value="exactly-one" />
    <action id="regimenEntry-290711-Example"><code><text value="regimen entry" />
        </code>
        <action id="Example-403017"><code><text value="dosage instruction group" />
        </code>
        <selectionBehavior value="exactly-one" />
        <action id="Example-403017-1"><code> <text value="dosage instruction" />
            </code>
            <type>
                <system value="http://h17.org/fhir/action-type" /> <code
                    value="create" />
            </type>
            <definition>
                    <reference value="Example" />
            </definition>
        </action>
        </action>
    </action>
</action>
``` treatment plan templates related to the specific type of cancer. The research institute periodically updates the treatment plan templates in its server based on current research In order to identify Regimen entry groups from above mentioned example, a combination of regular expression may be used. For example:

```
regimen_groups = regimen.findChildren('action', {'id': re.compile('^regimenEntryGroup-')})
for grp in regimen_groups:
regimen_entries = grp.findChildren('action', {'id': re.compile('^regimenEntry-')})
``` on the specific disease. In response to the query, the data source provides raw data related to the treatment plan templates. The raw data may include text information. The text information included in the raw data may include a large quantity of information and may be unstructured and randomly positioned within the raw data. Further, the raw data may be available in a pre-defined format, such as an Extensible Markup Language (XML) format, a Hypertext Markup Language (HTML) format, a Portable Document Format (PDF) format, etc.

The raw data is parsed, and tags are identified from the parsed raw data. The tags may be present in the raw data in form of headings, such as a name of a regime. Further, the tags are utilized for extracting elements required for preparing treatment plan from the raw data. The elements indicate specific information required for treating the patient. Examples of the elements may include medications, cycle definitions, dosing, frequency, routes of administration, pre-medication, and/or notes towards the treatment. The elements are identified in the raw data using complex regular expressions and a standard set of keywords. The complex regular expressions and the standard set of keywords may be pre-defined. The complex regular expressions may include a sequence of characters that defines a search pattern. The {'id': re.compile('^regimenEntryGroup-')} is a dictionary specifying the attributes within the tag. The above-mentioned algorithm searches the tags with an id attribute that matches the regular expression ^regimenEntryGroup-. For example the algorithm finds all elements with the tag name 'action' and an id attribute that matches the specified regular expressions, first looking for elements whose id starts with "regimenEntryGroup-" and then finding elements whose id starts with "regimenEntry-" within each of those groups. Using similar regular expression details nested regimenEntry is retrieved from each regimen entry group that contains information like drug ID, group ID, selectable, etc.

In another example, a regular expression "rx_route=re.compile(fr'({'IV|PO'})')" creates a regular expression pattern that matches either 'IV' or 'PO' and compiles it into a regular expression object stored in the variable rx_route. This can be used later for pattern-matching operations, such as assigning these details to corresponding medication or premedication.

The extracted elements may be utilized to construct formatted data. In an implementation, the formatted data may be presented in a Java Script Object Notation (JSON) format that is a machine-readable format. To create the JSON format, several parsing functions are employed to extract relevant information from a combination of HTML and XML elements obtained from the data source. The parsing functions may include a template definition parsing function, a regimen parsing function, and a medication and pre-medication parsing function.

In the template parsing function, the combination of HTML and XML elements obtained from the data source are utilized for extracting template definitions, such as template-Code, templateTitle, and regimenTitle. The template definitions are extracted using a library, such as Beautiful Soup. In the regimen parsing function, regimen details including relationships, medications, and their definitions are parsed from the combination of HTML and XML elements obtained from the data source. The function further parses through the regimen options for extracting related actions and medications. The regimen details, such as regimenId, definition, relations, selectable, and medicines are utilized to build a JSON object. In the medication and pre-medication codeId, drugName, dosage, route, timing, notes, safety parameters, and pre-medication details.

The parsed regimen and medication JSON objects are combined into a JSON structure. The JSON structure includes regimens and medications. In addition, the JSON structure includes a list of unique pre-medication JSON objects under the pre-medications. The JSON structure is accessible by applications pertaining to the healthcare system. Thus, the formatted data may be reusable and utilized by an application external to the system.

In some embodiments, the elements may be arranged in a hierarchical structure within the formatted data. The data arrangement in the hierarchical structure involves organizing the template data parsed from an Excel file into XML content for medications. Following is the hierarchical structure and example:

```
<KNOWLEDGEPLAN>
    <NEWFORMAT>1</NEWFORMAT>
    <SOURCEORDERSETTYPE>MULTIPLAN</SOURCEORDERSETTYPE>
    <CAPTION> </CAPTION>
    <!-- Other top-level elements -->
    <ORDERSETLIST>
        <ORDERSET>
            <CAPTION>Chemotherapy</CAPTION>
            <DURATION>28</DURATION>
            <DURATIONUNITMEAN>day</DURATIONUNITMEAN>
            <!-- Other attributes for Chemotherapy -->
            <PHASERELTNLIST>
                <PHASERELTN>
                    <TPHASEDESC>Prescriptions</TPHASEDESC>
            </PHASERELTNLIST>
            <COMPONENTLIST>
                <COMPONENT>
                    <CAPTION> Pre-Medications</CAPTION>
                    <!-- Other attributes for Pre-Medications -->
                    <SENTENCELIST>
                        <SENTENCE>
                            <!-- Other details for the sentence -->
                        </SENTENCE>
                    </SENTENCELIST>
                </COMPONENT>
                <COMPONENT>
                    <CAPTION>Treatment Regimen</CAPTION>
                    <!-- Other attributes for Treatment Regimen -->
                </COMPONENT>
    <COMPONENT>
                    <CAPTION>Medication components</CAPTION>
                    <!-- Other attributes for Medication components -->
                </COMPONENT>
        </ORDERSET>
        <ORDERSET>
            <CAPTION>Prescriptions</CAPTION>
            <!-- Other attributes for Prescriptions -->
            <COMPONENTLIST>
                <!-- components for medications and premedications-->
            </COMPONENTLIST>
        </ORDERSET>
        <!-- Additional ORDERSET elements -->
    </ORDERSETLIST>
</KNOWLEDGEPLAN>
``` parsing function, medication details, such as dosage, route, timing, notes, and safety parameters are parsed from the combination of HTML and XML elements obtained from the data source. In addition, medication information, such as drug ID, code ID, drug name, dosage details, route details, timing details, notes, and safety parameters are extracted from the combination of HTML and XML elements obtained from the data source. Further, pre-medication details are handled by parsing them separately, then merging them into the medication JSON object. The medication details are combined with the JSON object including drugId, In the above-mentioned algorithm, the XML structure starts with a root element "<KNOWLEDGEPLAN>". Within <KNOWLEDGEPLAN>, there are various sub-elements such as <NEWFORMAT>, <SOURCEORDERSETTYPE>, <CAPTION>, and <EVIDENCEURL>, each representing different metadata about the knowledge plan. Under <KNOWLEDGEPLAN>, there exists an <ORDERSETLIST> tag, containing multiple <ORDERSET> elements representing different sections. Within <ORDERSETLIST>, the first section is "Chemotherapy" that the pre-medications and medications. All the premedication components are followed by the pre-medication component tag and all the medications are followed by the treatment regimen tag. The "Chemotheraphy" section includes medications and pre-medications, with relationships indicated by <AND> and <OR> components. Multiple order sets under one medication are represented as nested <SENTENCE> tags under that medication.

After the chemotherapy regimen, the algorithm includes "Prescriptions" section. The "Prescription" section includes medications or pre-medications with the RX route as 'PO'. Like the chemotherapy section, relationships are indicated using <AND> and <OR> components. <AND> and <OR> components are represented as <COMPONENT> elements with the <CAPTION> indicating "AND" or "OR". Each component includes various attributes providing additional details. Medications and Pre-medications are nested within their respective sections and are represented as individual XML elements. Each medication element includes details, such as drug name, dosage, route, frequency, and other relevant information. Attributes within medication elements represent specific characteristics of the medication, such as drug ID, code ID, and group ID. Relationships between medications, such as those with the same regimen part or group ID, are maintained through the hierarchical structure and reflected in the XML organization. Comments and notes associated with medications are included as elements or attributes within the XML hierarchy, providing additional context or information.

The hierarchical structure allows for the organization and representation of template data in a clear and structured manner, facilitating further processing and utilization within the application. The structured data includes multiple data frames. Each data frame of the multiple data frames includes information related to a particular phase of a treatment schedule proposed in a treatment plan template. For example, once the JSON response containing all elements is prepared, the JSON response may be utilized to create multiple separate data frames. In some embodiments, the JSON response may include a regimen section, a medications section, and a premedication section. The data frames are prepared following health information system standards preserving the hierarchy of the elements. Along with all the elements, several other information, such as additional notes, special instructions, relation with other medicines, and all other available options are also stored in the data frames. In an example, the treatment plan templates may be segregated into three data frames, such as regimen parts, medications, and premedication. The data frames are then arranged into multiple sheets and these three sheets are combined to form structured data in natural language format, for example a spreadsheet.

The structured data may be provided to a medical provider for review. The medical provider may be a clinician, a doctor, a consultant, a care provider, or any end user. The structured data is provided to the medical provider through a user device associated with the medical provider. In some embodiments, the user device may include a user interface for rendering the structured data to the medical provider.

The medical provider may provide an update in the structured data through the user device. The update is received when the medical provider wants a deviation in existing schedule in the treatment plan template. For example, the medical provider may want to change the schedule of treatment for the patient. More particularly, the medical provider may want to continue the treatment for a number of days more than the number of days specified in the treatment plan template. In such scenario, the medical provider may update the structured data to increase the number of days of the treatment.

The structured data is updated by incorporating the update into the structured data to generate treatment plans. The treatment plans are generated in the machine-readable format or the natural language format. For example, the treatment plans are generated in XML format or in JSON format.

As described heretofore, the present disclosure provides a medical assistance system for generating treatment plans for treating the patient. In this regard, embodiments of the invention enable the medical assistance system to convert the raw data obtained from the data source into a standard format (machine readable format) and to generate a document having the elements. The document generated by the medical assistance system is easily understandable by the medical provider. The invention further enables the medical assistance system to accept the modification in the treatment plan suggested by the medical provider and to provide personalized treatment plan according to the medical condition of the user.

FIG. 1 illustrates an example of a medical assistance system 100 for constructing treatment plans for a patient according to an embodiment of the present invention. The medical assistance system 100 illustrates an exemplary block diagram of functional and/or structural components of a system employing natural language processing algorithms extract the templates and generate treatment plans according to medical provider's review. Medical assistance system 100 includes a data processing engine 102 for processing information received from a data source. The data processing engine 102 performs a part and/or all functionalities of the medical assistance system 100. The data processing engine 102 may represent any single computing system with dedicated hardware and software, multiple computing systems clustered together (e.g., a server farm), a portion of shared resources on one or more computing systems (e.g., virtual server), or any combination thereof. The data processing engine 102 may be composed of one or more general purpose computers, specialized server computers (including, by way of example, PC (personal computer) servers, Unpieced Information Computing System (UNIX®) servers, mid-range servers, mainframe computers, rack-mounted servers, etc.), server farms, server clusters, or any other appropriate arrangement and/or combination. The data processing engine 102 can include one or more virtual machines running virtual operating systems, or other computing architectures involving virtualization such as one or more flexible pools of logical storage devices that can be virtualized to maintain virtual storage devices for the server. In various embodiments, the data processing engine 102 may be adapted to run one or more services or software applications that provide the functionality described in the foregoing disclosure.

In some embodiments, the data processing engine 102 includes a software stack 104, which operates in the cloud, as a distributed system on a virtualization layer within the data processing engine 102. The software stack 104 includes an operating system 106. The operating system 106 may be implemented as a platform in the cloud, and which can host a number of services, such as input/output services 108, computation services 110, and display services 112. Each service is programmed to perform specific function. For example, the input/output services 108 allow data transfer from or to the data processing engine 102, the computation services 110 enable the data processing engine 102 to perform different computations in order to generate a treatment plan, and the display services 112 allow the data processing engine 102 to provide the data related to the treatment plan for rendering on a user device 124.

The data processing engine 102 is communicatively coupled to a network 114. Network 114 may comprise the Internet, and/or one or more public networks, private networks, other communications networks such as a cellular network, or similar network(s) for facilitating communication among devices connected through the network. In some embodiments, network 114 may be determined based on factors such as the source and destination of the information communicated over the network 114, the path between the source and destination, or the nature of the information. For example, intraorganizational or internal communication may use a private network or virtual private network (VPN). Moreover, in some embodiments, items shown communicatively coupled to the network 114 may be directly communicatively coupled to other items shown communicatively coupled to the network 114.

The network 114 may be any type of network familiar to those skilled in the art that can support data communications using any of a variety of available protocols, including without limitation TCP/IP (transmission control protocol/Internet protocol), SNA (systems network architecture), IPX (Internet packet exchange), AppleTalk®, and the like. Merely by way of example, network(s) 9010 can be a local area network (LAN), networks based on Ethernet, Token-Ring, a wide-area network (WAN), the Internet, a virtual network, a virtual private network (VPN), an intranet, an extranet, a public switched telephone network (PSTN), an infra-red network, a wireless network (e.g., a network operating under any of the Institute of Electrical and Electronics (IEEE) 1002.11 suite of protocols, Bluetooth®, and/or any other wireless protocol), and/or any combination of these and/or other networks.

The data processing engine 102 queries the data source 116 for treatment plan templates through an Application Programming Interface (API). As shown in FIG. 1, the query may be transmitted to a first data source 116a, a second data source 116b, and/or a third data source 116c. In an embodiment, the data source 116 includes firms, corporate entities, research institutes, and private or public organizations related to a medical field. For example, the data source may be a server associated with the National Comprehensive Cancer Network® (NCCN®).

The query may be transmitted based on a medical condition of a patient. The medical condition of the patient may be acquired from an Electronic Health Record (EHR) system 118. The EHR system 118 stores all the healthcare data of the patient. The data processing engine 102 acquires the healthcare data from the EHR system 118 and determines the medical condition of the patient based on the healthcare data.

Further, the data processing engine 102 acquires raw data related to the treatment plan templates from the multiple data sources 116 through the API. The raw data may include text information. The text information included in the raw data may be unstructured and randomly positioned in the raw data. Further, the raw data may be available in any format, such as an XML format, a HTML format, a PDF format, etc.

Data processing engine 102 parses the raw data and identifies the tags present in the raw data. The tags may be present in the raw data in form of headings, such as a name of a regime. In some embodiments, the tags include a Unique Identification Number (UIN) or Universal Unique Identifier (UUID) that are generated programmatically. Further, the tags are utilized for extracting the elements for preparing treatment plan from the raw data. The elements indicate specific information required for treating the patient. Examples of the elements may include medications, cycle definitions, dosing, frequency, routes of administration, premedication, and/or notes towards the treatment. The elements are identified in the raw data using complex regular expressions and a standard set of keywords related to the medical field.

The complex regular expression and the standard set of keywords are dynamically updated in real time. Such expressions and keywords are terms which are generally utilized in oncological studies. Further, data processing engine 102 extracts the elements from the raw data based on the complex regular expressions and the standard set of keywords.

The data processing engine 102 may construct formatted data based on the extracted elements. The elements may be arranged in a hierarchical structure within the formatted data. In an implementation, the formatted data may be presented in a JSON format. The JSON format is accessible by applications pertaining to a healthcare system and/or a health information system. Thus, the formatted data may be usable and utilized by an application external to the medical assistance system 100.

The data processing engine 102 utilizes the formatted data to generate structured data. The structured data includes multiple data frames. The formatted data is constructed using headings present in the text information of the raw data. Each data frame of the multiple data frames includes information related to a particular phase of a treatment schedule proposed in the treatment plan templates. For example, once the JSON response containing all elements is prepared, the JSON response may be utilized to create multiple separate data frames. In some embodiments, the structured data may include regimen parts, medications section, and premedication section. The data frames are prepared following health information system standards preserving the hierarchy of the extracted data. Along with all the elements, several other information, such as additional notes, special instructions, relation with other medicines, and all other available options are also stored in the data frames. In an example, the treatment plan templates may be segregated into three data frames, such as regimen parts, medications, and premedication. The data frames are then arranged into multiple sheets and these three sheets are combined to form structured data in natural language format, for example a spreadsheet.

The data processing engine 102 provides the structured data to a medical provider 122 for review. The medical provider 122 may be a clinician, a doctor, a consultant, a care provider, or any end user. The structured data is provided to the medical provider 122 through a user device 124 associated with the medical provider 122. In some embodiments, the user device 124 may include a user interface for rendering the structured data to the medical provider 122.

The user device 124 may include various types of computing systems such as Personal Assistant (PA) devices, portable handheld devices, general purpose computers such as personal computers and laptops, workstation computers, wearable devices, gaming systems, thin clients, various messaging devices, sensors or other sensing devices, and the like. These computing devices may run various types and versions of software applications and operating systems (e.g., Microsoft Windows®, Apple Macintosh®, UNIX® or UNIX-like operating systems, Linux or Linux-like operating systems such as Google Chrome™ OS) including various mobile operating systems (e.g., Microsoft Windows Mobile®, iOS®, Windows Phone®, Android™, Black-Berry®, Palm OS®). Portable handheld devices may include cellular phones, smartphones, (e.g., an iPhone®), tablets (e.g., iPad®), personal digital assistants (PDAs), and the like. Wearable devices may include Google Glass® head-mounted displays and other devices. Gaming systems may include various handheld gaming devices, Internet-enabled gaming devices (e.g., a Microsoft Xbox® gaming console with or without a Kinect® gesture input device, Sony PlayStation® system, various gaming systems provided by Nintendo®, and others), and the like. The user device 124 may be capable of executing various applications such as various Internet-related apps and communication applications (e.g., E-mail applications, short message service (SMS) applications) and may use various communication protocols.

The user device 124 may include a screen or display for rendering the user interface that includes the structured data. The medical provider 122 may edit the elements rendered on the user interface to provide an update in the treatment plan templates. The update is based on a deviation/update or an error in existing schedule provided in the treatment plan templates. In some embodiments, the medical provider 122 may want to change the schedule of treatment for the patient. In such scenario, the medical provider 122 may update the structured data according to their requirement.

The data processing engine 102 receives the update from the medical provider 122 through the network 114. The structured data is updated by incorporating the update into the structured data to generate treatment plans. The treatment plans are generated in the machine-readable format or the natural language format. For example, the treatment plans are generated in XML format or in JSON format.

In some embodiments, the medical provider 122 may identify errors in the structured data while reviewing the treatment plan templates included in the raw data. The medical provider 122 may update the structured data through the user interface rendered on the user device 124. Further, the data processing engine 102 may update the treatment plans based on the updated structured data.

Figure 2:
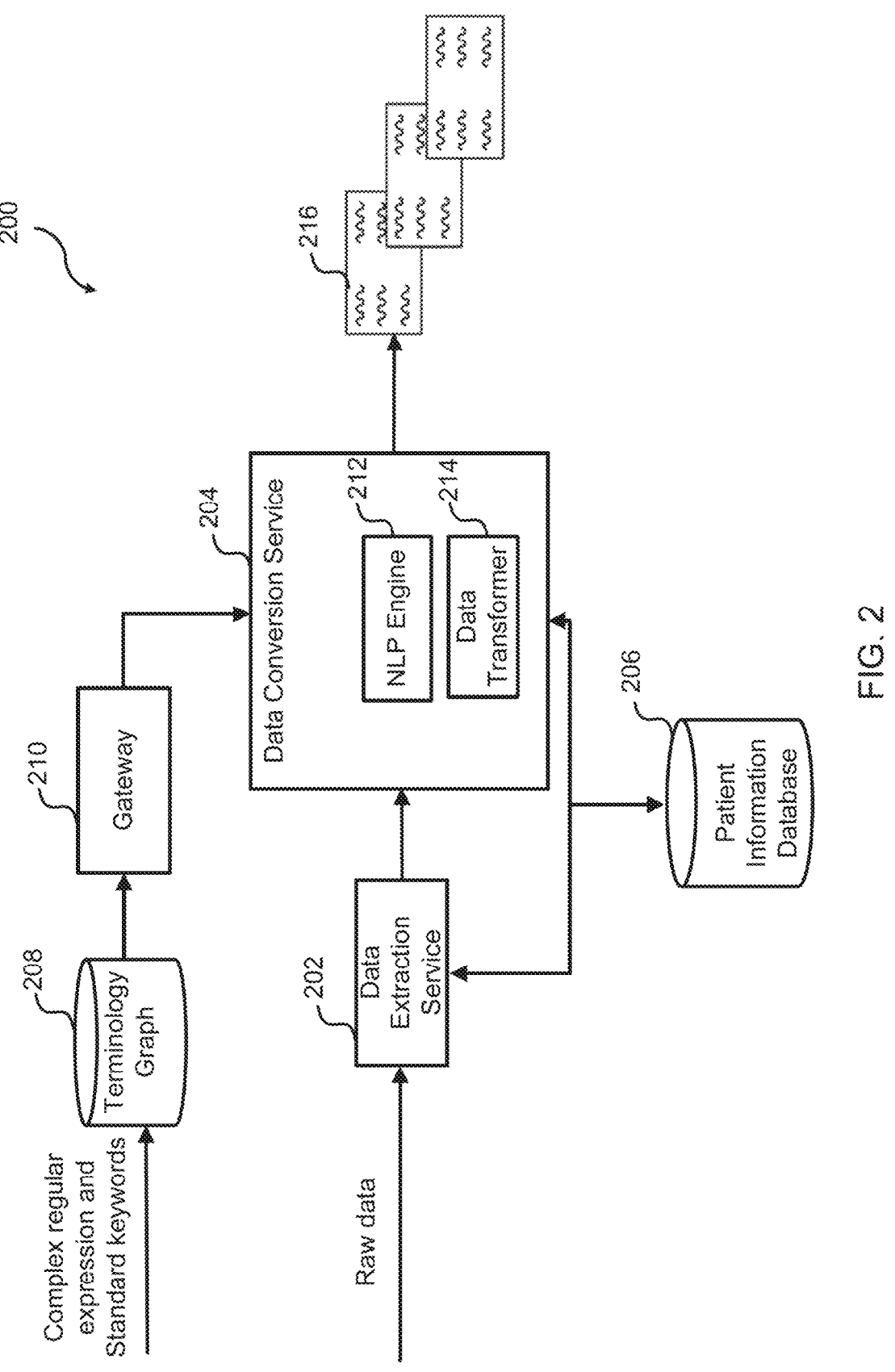
FIG. 2 illustrates an example computing architecture of a computerized system according to an embodiment of the present invention.

FIG. 2 illustrates an example computing architecture 200 of a computerized system according to an embodiment of the present invention. The system includes a data extraction service 202, a data conversion service 204, a patient information database 206, a terminology graph 208, and a gateway 210.

The data extraction service 202 queries a data source, such as a research institute for treatment plan templates. In response to the query, the data extraction service 202 receives raw data from the data source. The raw data may be received using an API running on a user platform, such as a mobile device. The query may be generated based on a medical condition of a patient. The medical condition of the patient may be determined using data received from the patient information database 206. The patient information database 206 stores the healthcare data of the patient. The healthcare data also includes historical events of a patient's health and details on the historical events.

The data extraction service 202 provides the raw data to the data conversion service 204. The raw data may include text information. The text information included in the raw data may be unstructured and randomly positioned in the raw data. Further, the raw data may be available in any format, such as an XML format, a HTML format, a PDF format, etc.

Terminology graph 208, as used herein, is an organizational graph comprising inter-relationships of a plurality of terms. The relationship generally includes at least a clinical term, complex regular expression, and a standard set of keywords. The set of keywords may include prescriptions, drugs, a medical condition, etc. For instance, diabetes (a clinical condition) may be listed along with medications (insulin) that are used to treat diabetes. Additionally, the complex regular expression and keywords related to a disease, such as cancer may be stored in terminology graph 208. Additionally, terminology graph 208 may be dynamically updated in real time. Terminology graph 208 provides the complex regular expression and the standard set of keywords to the data conversion service 204 through gateway 210.

The gateway 210 provides a connection between the terminology graph 208 and the data conversion service 204. The gateway 210 communicatively connects the terminology graph 208 to the data conversion service 204. In particular, the terminology graph 208 is accessible, via the gateway 210 to, for instance, the data conversion service 204.

The data conversion service 204 includes a Natural Language Processing (NLP) engine 212 that parses the raw data and identifies the tags within the raw data. The tags may be present in the raw data in form of headings, such as a name of a regime. The tags include a UIN or UUID that are generated programmatically. Further, the tags are utilized for extracting elements from the raw data. The elements indicate specific information required for treating the patient. Examples of the elements may include medications, cycle definitions, dosing, frequency, routes of administration, pre-medication, and/or notes towards the treatment. The elements are identified in the raw data using complex regular expressions and a standard set of keywords.

Further, the complex regular expressions and the standard set of keywords are stored in the terminology graph 208. NLP engine 212 loads the complex regular expressions and the standard set of keywords from the terminology graph 208 through the gateway 210. The NLP engine 212 may include multiple NLP engines and the NLP engines may be disparate. Further, the NLP engine 212 extracts the elements required for preparing treatment plan from the raw data based on the complex regular expressions and the standard set of keywords.

The data processing engine 102 further includes a data transformer 214 that obtains the extracted elements from the NLP engine 212. The data transformer 214 constructs formatted data using the extracted elements. The elements may be arranged in a hierarchical structure within the formatted data. The hierarchical structure may include an order in which the treatment plans are implemented, or an order in which prescriptions are provided to a patient. In an implementation, the formatted data may be presented in a JSON format. The JSON format is accessible by applications pertaining to the healthcare system.

The data transformer 214 utilizes the formatted data to generate structured data. The structured data includes multiple data frames. Each data frame of the multiple data frames includes information related to a particular phase of a treatment schedule proposed in the treatment plan templates. In some embodiments, the structured data may include regimen parts, medications section, and premedication section. The data frames are prepared following health information system standards preserving the hierarchy of the extracted data. Along with all the elements details regarding additional notes, special instructions, relation with other medicines, and all other available options are also stored in the data frames. Further, data transformer 214 converts the data frames into multiple sheets and combines these multiple sheets to form structured data. In some implementations, the structured data is present in the natural language format, for example a spreadsheet. The data conversion service 204 provides the structured data to the user device 124.

The user device 124 may include a screen for rendering a graphical user interface 216 that includes the structured data. The medical provider 122 may edit the details rendered on the user interface to provide an update in the treatment plan templates. The update is based on a deviation/update or an error in existing schedule provided in the treatment plan templates. In some embodiments, the medical provider 122 may want to change the schedule of treatment for the patient. For example, the medical provider 122 may want to continue the treatment for a number of days more than the number of days specified in the treatment plan template. Medical provider 122 may update the structured data according to their requirement.

The structured data is updated by incorporating the update into the structured data to generate new treatment plans. The treatment plans are generated in the machine-readable format or the natural language format. For example, the treatment plans are generated in XML format or in JSON format.

FIG. 3 illustrates an exemplary document 300 illustrating raw data according to an embodiment of the present invention. Document 300 is extracted from a server of a research institute, such as a NCCN® server. Document 300 may be fetched by querying one or more template codes through the API. For example, the document shown in FIG. 3 is fetched by querying REC11. The treatment plan template related to REC11 is fetched from the NCCN® server.

Document 300 is parsed by the data processing engine 102 and tags present within the document 300 are identified. For example, element 306a indicates a tag that is a heading "chemotherapy regimen". Details of the heading "chemotherapy regimen" are provided under the tag. Another tag is identified as the heading "supportive care" is represented by element 306b. Data processing engine 102 passes through document 300 and identifies all the tags present in the document 300.

FIG. 4A illustrates another exemplary document 400 illustrating raw data according to an embodiment of the present invention. Document 400 represents a treatment plan template for treating breast cancer, as illustrated in element 402 of FIG. 4A. Element 404 indicates a tag referring chemotherapy regimen for breast cancer. Further, element 406 indicates a tag referring schedule of the treatment to be performed by the medical provider 122. Elements 408a and 408b indicate different options for treatment of breast cancer.

Figure 4C:
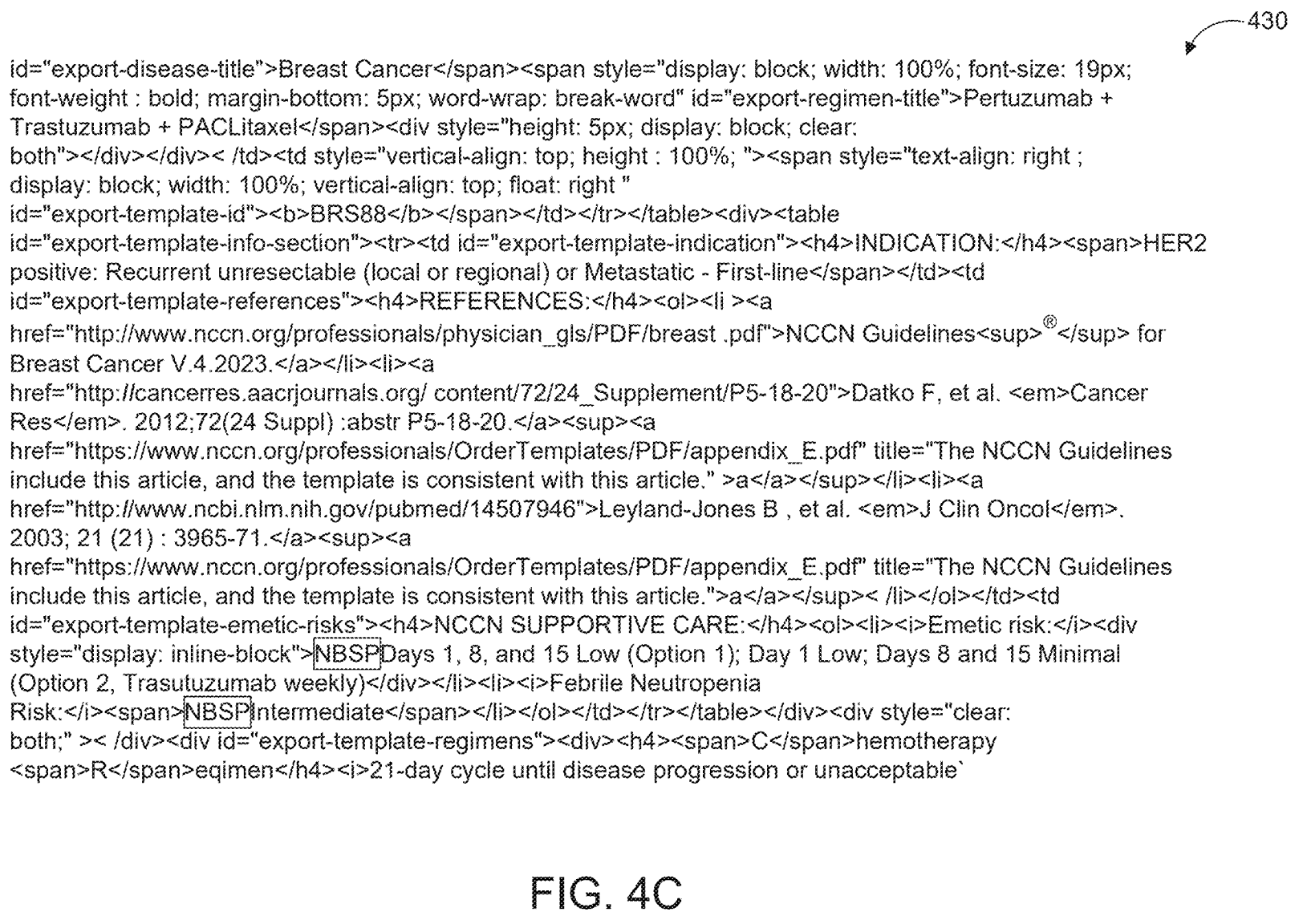

FIGS. 4B and 4C illustrate an exemplary formatted data 420 and 430 according to the present invention. The formatted data is obtained from document 400. The formatted data includes elements extracted from the tags using the complex regular expression and the standard set of keywords. The elements are arranged in a hierarchical manner within the formatted data. The elements include all the relevant information required for the treatment of the patient.

Figure 5A:
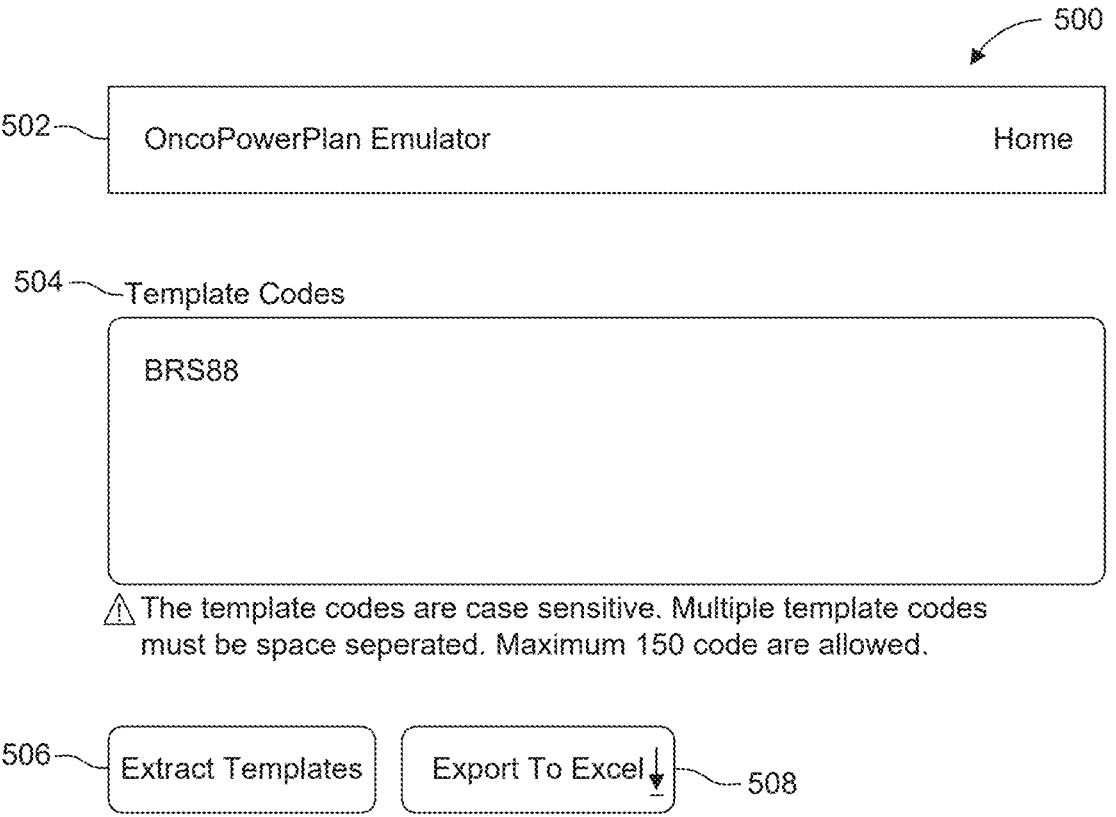

FIGS. 5A-5C illustrate a graphical user interface (GUI) according to an embodiment of the present invention. As illustrated in FIG. 5A, the user device 124 renders a user interface 500 on the device screen of the medical assistance system 100. The user interface 500 includes element 502 that indicates a name of the software of the medical assistance system 100 such as the OncoPowerPlan Emulator. The user interface 500 further includes element 504 for providing an option to enter template code associated with one or more disease of the patient. The user may enter one or more template codes into element 504. Post entering the template code, the user may select element 506 for searching the treatment plan templates through the API. Once the user selects element 506, a server associated with the research institute is queried for treatment plan templates for the disease related to the template code. Further, the raw data associated with the treatment plan templates is fetched through the API. The raw data may be parsed, and tags may be identified from the raw data.

Once the raw data is parsed and the tags are identified, the structured data is constructed. The user interface 500 provides element 506 to export the structured data into a spreadsheet. The spreadsheet may be downloaded in user device 124. The spreadsheet may include multiple data frames.

As illustrated in FIG. 5B, spreadsheet 510 may include a first frame indicating two different regimens for treating breast cancer. Each regimen may specify one or more of a template code, a template title, a caption, a regimen ID, definition of corresponding regimen, relations, and selectable. The medical provider 122 may select one or the regimens provided in the first frame.

As illustrated in FIG. 5C, spreadsheet 520 may include a second frame. The second frame includes details of each regimen. For example, the second frame may include names of drugs, dosage of each drug, schedule of each drug, and relation between different drugs. The second frame includes various options for treating the patient.

Figure 6:
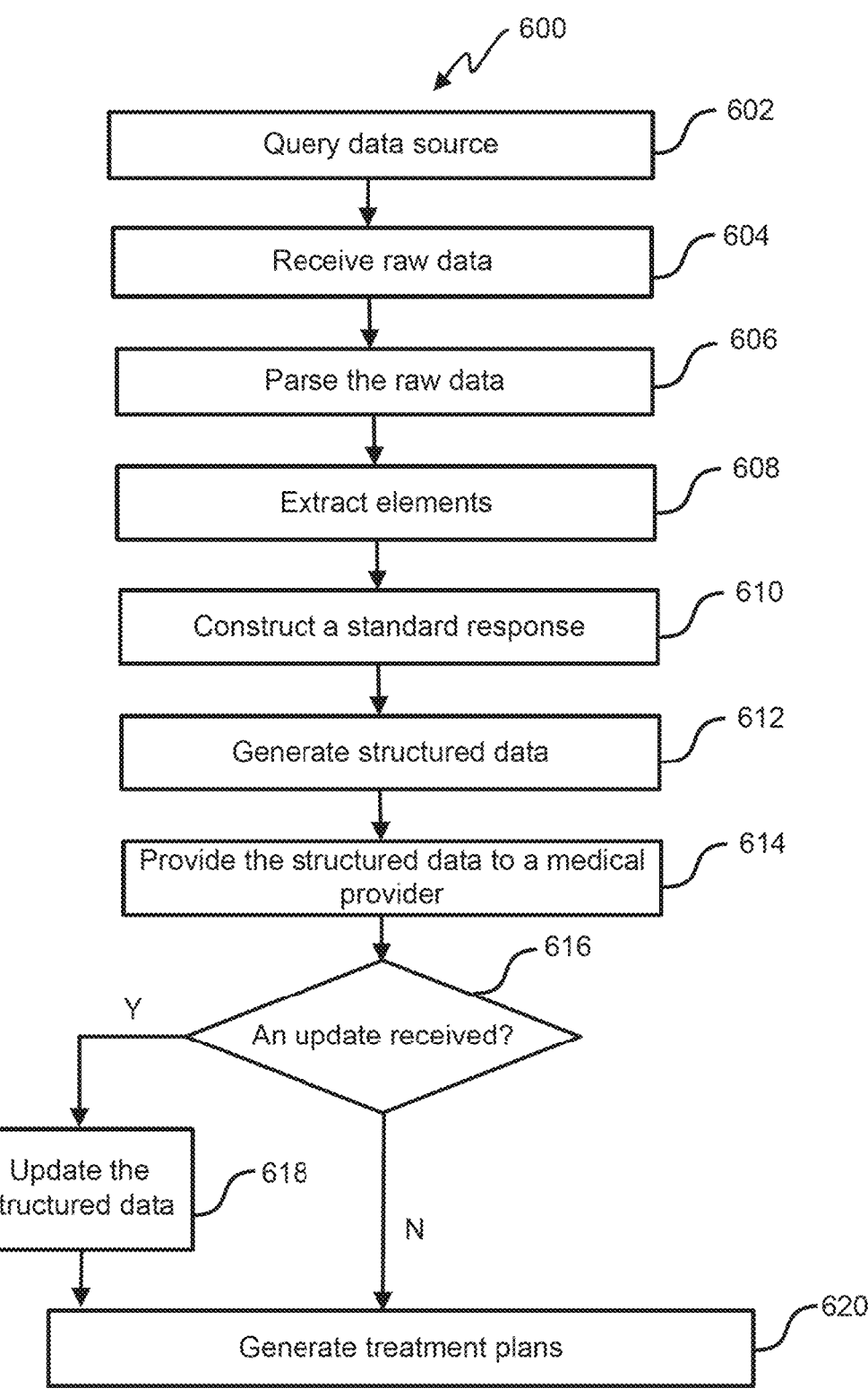
FIG. 6 illustrates a flowchart of process for generating treatment plans according to some embodiments of the invention.

FIG. 6 illustrates a flowchart of a process 600 for generating treatment plans according to some embodiments of the invention. The process 600 may be performed at least in part by any of the components described in the figures herein, for example, by the data processing engine 102. The process 600 can begin at block 602, where the data source is queried for treatment plan templates. The data source is queried based on the medical condition of a patient.

At block 604, the raw data is received from the data source in response to the query. The raw data may be received using an API running on a user platform, such as a mobile device. The raw data may include text information. The text information included in the raw data may be unstructured and randomly positioned in the raw data. Further, the raw data may be available in any format, such as an XML format, a HTML format, a PDF format, etc.

At block 606, the raw data is parsed, and tags are identified from the raw data. The tags may be present in the raw data in the form of headings, such as a name of a regime. The tags include a UIN or UUID that are generated programmatically. Further, the tags are utilized for extracting elements from the raw data. The elements may include relevant details associated with each tag. For example, if a tag related to chemotherapy regimen is identified, the details (elements) of the chemotherapy regimen may be extracted from the raw data. The details may include name of drugs and dosage of the drugs.

At block 608, the elements are extracted from the tags. The elements may be extracted using the complex regular expression and the standard set of keywords. The standard set of keywords relate to the medical field. The complex regular expression and the standard set of keywords are obtained from a terminology graph through a gateway. The elements includes details of dosage, drugs, schedule of treatment, duration between two drugs, compositions of drugs, etc.

At block 610, the formatted data is constructed. The formatted data is constructed based on the extracted elements. The elements may be arranged in a hierarchical structure within the formatted data. In an implementation, the formatted data may be presented in a JSON format. The JSON format is accessible by applications pertaining to the healthcare system.

At block 612, the structed data is generated based on the formatted data. The structed data includes multiple data frames. Each data frame of the multiple data frames includes information related to a particular phase of a treatment schedule proposed in the treatment plan templates. In some embodiments, the structured data may include regimen parts, medications section, and premedication section. The data frames are prepared following health information system standards preserving the hierarchy of the extracted data. Along with the elements, details regarding additional notes, special instructions, relation with other medicines, and other available options are also stored in the data frames. Further, the data frames are converted into multiple sheets and these multiple sheets are combined to form structured data. In some implementations, the structured data is present in the natural language format, for example a spreadsheet.

At block 614, the structured data is provided to the medical provider 122 for review. The structured data may be rendered on a graphical user interface of user device 124. Medical provider 122 is enabled to provide an update in the treatment plan templates. In some embodiments, the medical provider 122 may want to change the schedule of treatment for the patient. For example, the medical provider 122 may want to continue the treatment for a greater number of days compared to the number of days specified in the treatment plan template. The medical provider 122 may update the structured data according to the medical requirement.

At block 616, it is determined whether the update is received from the medical provider 122 or not. If the update is provided by the medical provider 122, the flow of process 600 moves to block 618. If the update is not provided by the medical provider 122, the flow of the process 600 moves to block 620.

At block 618, the structured data is updated based on the update/feedback provided by the medical provider 122. The structured data is updated by incorporating the feedback into the structured data.

At block 620, the treatment plans are generated based on the updating of the structured data. The treatment plans are generated in the machine-readable format or the natural language format. For example, the treatment plans are generated in XML format or in JSON format. Further, the treatment plans are utilized by the medical provider 122 to provide treatment to the patient.

Figure 7:
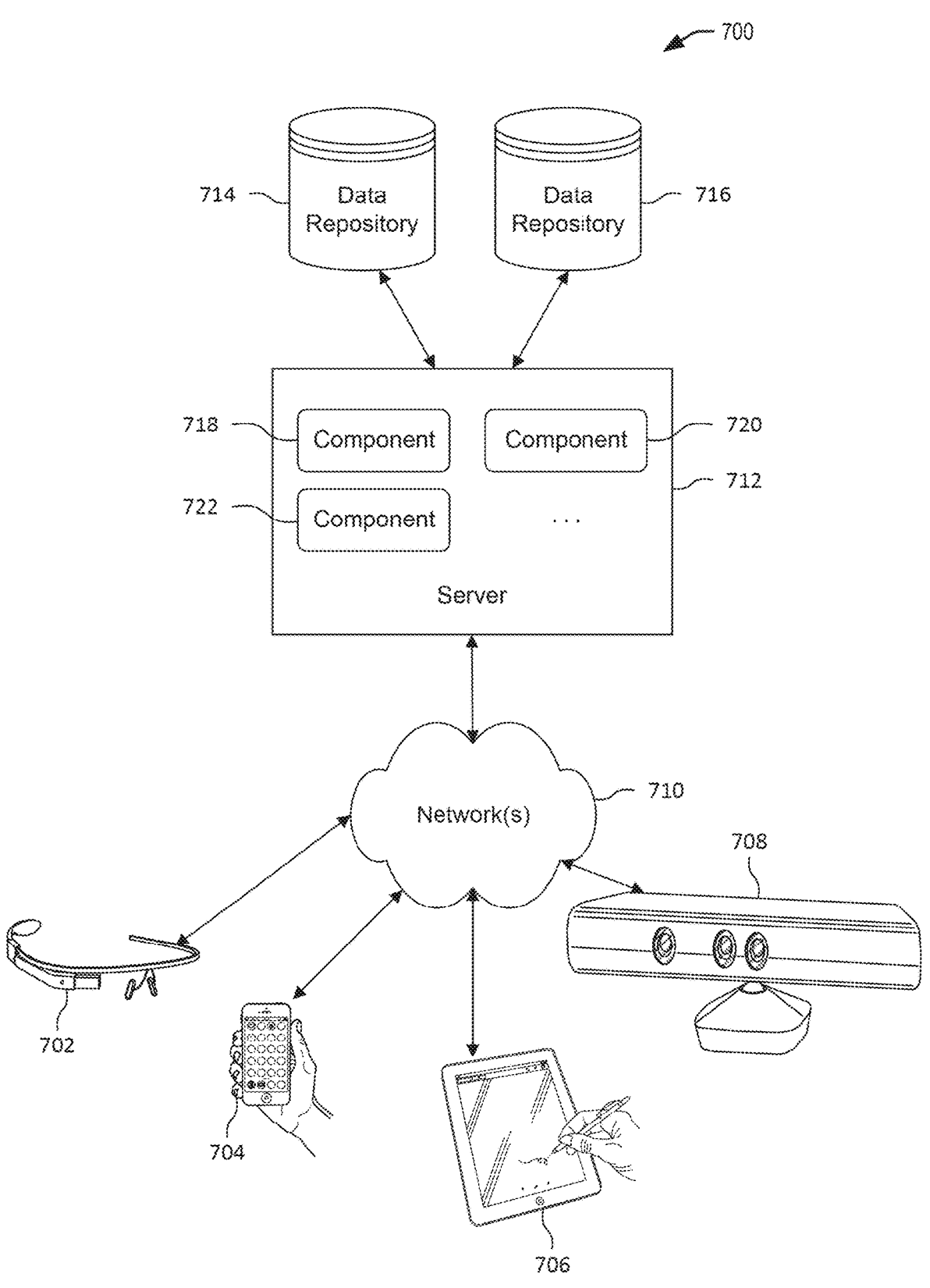
FIG. 7 depicts a simplified diagram of a distributed system for implementing certain aspects.

FIG. 7 depicts a simplified diagram of a distributed system 700 for implementing an embodiment. In the illustrated embodiment, distributed system 700 includes one or more client computing devices 702, 704, 706, and 708, coupled to a server 712 via one or more communication networks 710. Clients computing devices 702, 704, 706, and 708 may be configured to execute one or more applications.

In various aspects, server 712 may be adapted to run one or more services or software applications that enable techniques for handling long text for pre-trained language models.

In certain aspects, server 712 may also provide other services or software applications that can include non-virtual and virtual environments. In some aspects, these services may be offered as web-based or cloud services, such as under a Software as a Service (SaaS) model to the users of client computing devices 702, 704, 706, and/or 708. Users operating client computing devices 702, 704, 706, and/or 708 may in turn utilize one or more client applications to interact with server 712 to utilize the services provided by these components.

In the configuration depicted in FIG. 7, server 712 may include one or more components 718, 720 and 722 that implement the functions performed by server 712. These components may include software components that may be executed by one or more processors, hardware components, or combinations thereof. It should be appreciated that various different system configurations are possible, which may be different from distributed system 700. The embodiment shown in FIG. 7 is thus one example of a distributed system for implementing an embodiment system and is not intended to be limiting.

Users may use client computing devices 702, 704, 706, and/or 708 for techniques for handling long text for pre-trained language models in accordance with the teachings of this disclosure. A client device may provide an interface that enables a user of the client device to interact with the client device. The client device may also output information to the user via this interface. Although FIG. 7 depicts only four client computing devices, any number of client computing devices may be supported.

The client devices may include various types of computing systems such as portable handheld devices, general purpose computers such as personal computers and laptops, workstation computers, wearable devices, gaming systems, thin clients, various messaging devices, sensors or other sensing devices, and the like. These computing devices may run various types and versions of software applications and operating systems (e.g., Microsoft Windows® Apple Macintosh®, UNIX® or UNIX-like operating systems, Linux orf Linux-like operating systems such as Google Chrome™ OS) including various mobile operating systems (e.g., Microsoft Windows Mobile®, iOS®, Windows Phone®, Android™, BlackBerry®, Palm OS®). Portable handheld devices may include cellular phones, smartphones, (e.g., an iPhone®), tablets (e.g., iPad®), personal digital assistants (PDAs), and the like. Wearable devices may include Apple Vision Pro®, Ray-Ban® Meta Smart Glasses®, Google Glass® head mounted display, and other devices. Gaming systems may include various handheld gaming devices, Internet-enabled gaming devices (e.g., a Microsoft Xbox® gaming console with or without a Kinect® gesture input device, Sony PlayStation® system, various gaming systems provided by Nintendo®, and others), and the like. The client devices may be capable of executing various different applications such as various Internet-related apps, communication applications (e.g., E-mail applications, short message service (SMS) applications) and may use various communication protocols.

Network(s) 710 may be any type of network familiar to those skilled in the art that can support data communications using any of a variety of available protocols, including without limitation TCP/IP (transmission control protocol/Internet protocol), SNA (systems network architecture), IPX (Internet packet exchange), AppleTalk®, and the like. Merely by way of example, network(s) 710 can be a local area network (LAN), networks based on Ethernet, Token-Ring, a wide-area network (WAN), the Internet, a virtual network, a virtual private network (VPN), an intranet, an extranet, a public switched telephone network (PSTN), an infra-red network, a wireless network (e.g., a network operating under any of the Institute of Electrical and Electronics (IEEE) 1002.11 suite of protocols, Bluetooth®, and/or any other wireless protocol), and/or any combination of these and/or other networks.

Server 712 may be composed of one or more general purpose computers, specialized server computers (including, by way of example, PC (personal computer) servers, UNIX® servers, mid-range servers, mainframe computers, rack-mounted servers, etc.), server farms, server clusters, or any other appropriate arrangement and/or combination. Server 712 can include one or more virtual machines running virtual operating systems, or other computing architectures involving virtualization such as one or more flexible pools of logical storage devices that can be virtualized to maintain virtual storage devices for the server. In various aspects, server 712 may be adapted to run one or more services or software applications that provide the functionality described in the foregoing disclosure.

The computing systems in server 712 may run one or more operating systems including any of those discussed above, as well as any commercially available server operating system. Server 712 may also run any of a variety of additional server applications and/or mid-tier applications, including HTTP (hypertext transport protocol) servers, FTP (file transfer protocol) servers, CGI (common gateway interface) servers, JAVA® servers, database servers, and the like. Exemplary database servers include without limitation those commercially available from Oracle®, Microsoft®, Sybase®, IBM® (International Business Machines), and the like.

In some implementations, server 712 may include one or more applications to analyze and consolidate data feeds and/or event updates received from users of client computing devices 702, 704, 706, and 708. As an example, data feeds and/or event updates may include, but are not limited to, Twitter® feeds, Facebook® updates or real-time updates received from one or more third party information sources and continuous data streams, which may include real-time events related to sensor data applications, financial tickers, network performance measuring tools (e.g., network monitoring and traffic management applications), clickstream analysis tools, automobile traffic monitoring, and the like. Server 712 may also include one or more applications to display the data feeds and/or real-time events via one or more display devices of client computing devices 702, 704, 706, and 708.

Distributed system 700 may also include one or more data repositories 714, 716. These data repositories may be used to store data and other information in certain aspects. For example, one or more of the data repositories 714, 716 may be used to store information for techniques for handling long text for pre-trained language models (e.g., intent score, overall score). Data repositories 714, 716 may reside in a variety of locations. For example, a data repository used by server 712 may be local to server 712 or may be remote from server 712 and in communication with server 712 via a network-based or dedicated connection. Data repositories 714, 716 may be of different types. In certain aspects, a data repository used by server 712 may be a database, for example, a relational database, such as databases provided by Oracle Corporation® and other vendors. One or more of these databases may be adapted to enable storage, update, and retrieval of data to and from the database in response to structured query language (SQL)-formatted commands.

In certain aspects, one or more of data repositories 714, 716 may also be used by applications to store application data. The data repositories used by applications may be of different types such as, for example, a key-value store repository, an object store repository, or a general storage repository supported by a file system.

Figure 8:
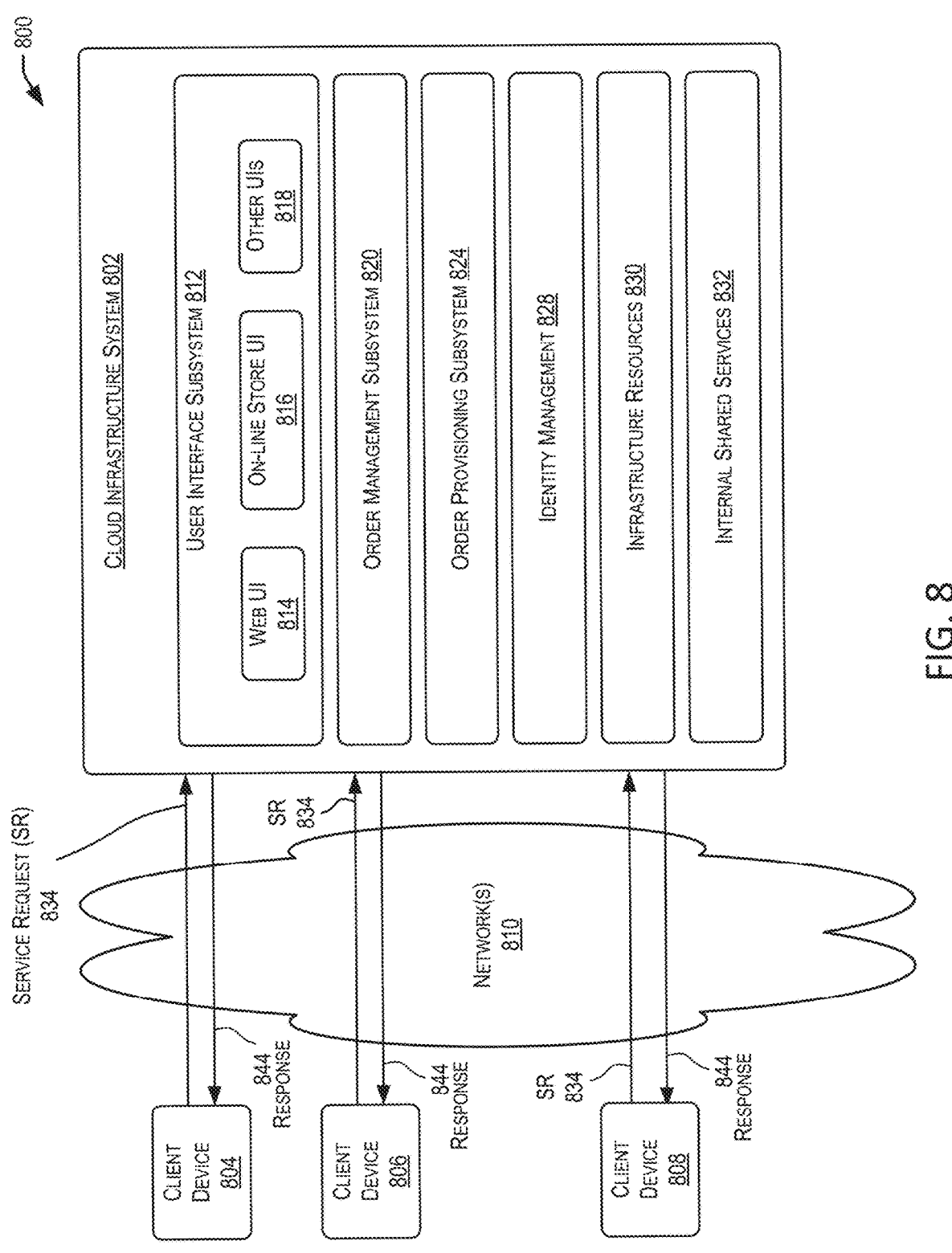
FIG. 8 is a simplified block diagram of one or more components of a system environment by which services provided by one or more components of an embodiment system may be offered as cloud services, in accordance with certain aspects.

In certain aspects, the techniques for handling long text for pre-trained language models functionalities described in this disclosure may be offered as services via a cloud environment. FIG. 8 is a simplified block diagram of a cloud-based system environment in which various text handling-related services may be offered as cloud services, in accordance with certain aspects. In the embodiment depicted in FIG. 8, cloud infrastructure system 802 may provide one or more cloud services that may be requested by users using one or more client computing devices 804, 806, and 808. Cloud infrastructure system 802 may comprise one or more computers and/or servers that may include those described above for server 712. The computers in cloud infrastructure system 802 may be organized as general purpose computers, specialized server computers, server farms, server clusters, or any other appropriate arrangement and/or combination.

Network(s) 810 may facilitate communication and exchange of data between clients 804, 806, and 808 and cloud infrastructure system 802. Network(s) 810 may include one or more networks. The networks may be of the same or different types. Network(s) 810 may support one or more communication protocols, including wired and/or wireless protocols, for facilitating the communications.

The embodiment depicted in FIG. 8 is only one example of a cloud infrastructure system and is not intended to be limiting. It should be appreciated that, in some other aspects, cloud infrastructure system 802 may have more or fewer components than those depicted in FIG. 8, may combine two or more components, or may have a different configuration or arrangement of components. For example, although FIG. 8 depicts three client computing devices, any number of client computing devices may be supported in alternative aspects.

The term cloud service is generally used to refer to a service that is made available to users on demand and via a communication network such as the Internet by systems (e.g., cloud infrastructure system 802) of a service provider. Typically, in a public cloud environment, servers and systems that make up the cloud service provider's system are different from the client's own on premise servers and systems. The cloud service provider's systems are managed by the cloud service provider. Clients can thus avail themselves of cloud services provided by a cloud service provider without having to purchase separate licenses, support, or hardware and software resources for the services. For example, a cloud service provider's system may host an application, and a user may, via a network 810 (e.g., the Internet), on demand, order and use the application without the user having to buy infrastructure resources for executing the application. Cloud services are designed to provide easy, scalable access to applications, resources, and services. Several providers offer cloud services. For example, several cloud services are offered by Oracle Corporation® of Redwood Shores, California, such as middleware services, database services, Java cloud services, and others.

In certain aspects, cloud infrastructure system 802 may provide one or more cloud services using different models such as under a Software as a Service (SaaS) model, a Platform as a Service (PaaS) model, an Infrastructure as a Service (IaaS) model, and others, including hybrid service models. Cloud infrastructure system 802 may include a suite of applications, middleware, databases, and other resources that enable provision of the various cloud services.

A SaaS model enables an application or software to be delivered to a client over a communication network like the Internet, as a service, without the client having to buy the hardware or software for the underlying application. For example, a SaaS model may be used to provide clients access to on-demand applications that are hosted by cloud infrastructure system 802. Examples of SaaS services provided by Oracle Corporation® include, without limitation, various services for human resources/capital management, client relationship management (CRM), enterprise resource planning (ERP), supply chain management (SCM), enterprise performance management (EPM), analytics services, social applications, and others.

An IaaS model is generally used to provide infrastructure resources (e.g., servers, storage, hardware, and networking resources) to a client as a cloud service to provide elastic compute and storage capabilities. Various IaaS services are provided by Oracle Corporation®.

A PaaS model is generally used to provide, as a service, platform and environment resources that enable clients to develop, run, and manage applications and services without the client having to procure, build, or maintain such resources. Examples of PaaS services provided by Oracle Corporation® include, without limitation, Oracle Java Cloud Service (JCS), Oracle Database Cloud Service (DBCS), data management cloud service, various application development solutions services, and others.

Cloud services are generally provided on an on-demand self-service basis, subscription-based, elastically scalable, reliable, highly available, and secure manner. For example, a client, via a subscription order, may order one or more services provided by cloud infrastructure system 802. Cloud infrastructure system 802 then performs processing to provide the services requested in the client's subscription order. Cloud infrastructure system 802 may be configured to provide one or even multiple cloud services.

Cloud infrastructure system 802 may provide the cloud services via different deployment models. In a public cloud model, cloud infrastructure system 802 may be owned by a third party cloud services provider and the cloud services are offered to any general public client, where the client can be an individual or an enterprise. In certain other aspects, under a private cloud model, cloud infrastructure system 802 may be operated within an organization (e.g., within an enterprise organization) and services provided to clients that are within the organization. For example, the clients may be various departments of an enterprise such as the Human Resources department, the Payroll department, etc. or even individuals within the enterprise. In certain other aspects, under a community cloud model, the cloud infrastructure system 802 and the services provided may be shared by several organizations in a related community. Various other models such as hybrids of the above mentioned models may also be used.

Client computing devices 804, 806, and 808 may be of different types (such as devices 702, 704, 706, and 708 depicted in FIG. 7) and may be capable of operating one or more client applications. A user may use a client device to interact with cloud infrastructure system 802, such as to request a service provided by cloud infrastructure system 802. For example, a user may use a client device to request a chat bot service described in this disclosure.

In some aspects, the processing performed by cloud infrastructure system 802 for providing Chabot services may involve big data analysis. This analysis may involve using, analyzing, and manipulating large data sets to detect and visualize various trends, behaviors, relationships, etc. within the data. This analysis may be performed by one or more processors, possibly processing the data in parallel, performing simulations using the data, and the like. For example, big data analysis may be performed by cloud infrastructure system 802 for determining the intent of an utterance. The data used for this analysis may include structured data (e.g., data stored in a database or structured according to a structured model) and/or unstructured data (e.g., data blobs (binary large objects)).

As depicted in the embodiment in FIG. 8, cloud infrastructure system 802 may include infrastructure resources 830 that are utilized for facilitating the provision of various cloud services offered by cloud infrastructure system 802. Infrastructure resources 830 may include, for example, processing resources, storage or memory resources, networking resources, and the like.

In certain aspects, to facilitate efficient provisioning of these resources for supporting the various cloud services provided by cloud infrastructure system 802 for different clients, the resources may be bundled into sets of resources or resource modules (also referred to as "pods"). Each resource module or pod may comprise a pre-integrated and optimized combination of resources of one or more types. In certain aspects, different pods may be pre-provisioned for different types of cloud services. For example, a first set of pods may be provisioned for a database service, a second set of pods, which may include a different combination of resources than a pod in the first set of pods, may be provisioned for Java service, and the like. For some services, the resources allocated for provisioning the services may be shared between the services.

Cloud infrastructure system 802 may itself internally use services 832 that are shared by different components of cloud infrastructure system 802 and which facilitate the provisioning of services by cloud infrastructure system 802. These internal shared services may include, without limitation, a security and identity service, an integration service, an enterprise repository service, an enterprise manager service, a virus scanning and white list service, a high availability, backup and recovery service, service for enabling cloud support, an email service, a notification service, a file transfer service, and the like.

Cloud infrastructure system 802 may comprise multiple subsystems. These subsystems may be implemented in software, or hardware, or combinations thereof. As depicted in FIG. 8, the subsystems may include a user interface subsystem 812 that enables users or clients of cloud infrastructure system 802 to interact with cloud infrastructure system 802. User interface subsystem 812 may include various different interfaces such as a web interface 814, an online store interface 816 where cloud services provided by cloud infrastructure system 802 are advertised and are purchasable by a consumer, and other interfaces 818. For example, a client may, using a client device, request (service request 834) one or more services provided by cloud infrastructure system 802 using one or more of interfaces 814, 816, and 818. For example, a client may access the online store, browse cloud services offered by cloud infrastructure system 802, and place a subscription order for one or more services offered by cloud infrastructure system 802 that the client wishes to subscribe to. The service request may include information identifying the client and one or more services that the client desires to subscribe to. For example, a client may place a subscription order for a Chabot related service offered by cloud infrastructure system 802. As part of the order, the client may provide information identifying for input (e.g., utterances).

In certain aspects, such as the embodiment depicted in FIG. 8, cloud infrastructure system 802 may comprise an order management subsystem (OMS) 820 that is configured to process the new order. As part of this processing, OMS 820 may be configured to: create an account for the client, if not done already; receive billing and/or accounting information from the client that is to be used for billing the client for providing the requested service to the client; verify the client information; upon verification, book the order for the client; and orchestrate various workflows to prepare the order for provisioning.

Once properly validated, OMS 820 may then invoke the order provisioning subsystem (OPS) 824 that is configured to provision resources for the order including processing, memory, and networking resources. The provisioning may include allocating resources for the order and configuring the resources to facilitate the service requested by the client order. The manner in which resources are provisioned for an order and the type of the provisioned resources may depend upon the type of cloud service that has been ordered by the client. For example, according to one workflow, OPS 824 may be configured to determine the particular cloud service being requested and identify a number of pods that may have been pre-configured for that particular cloud service. The number of pods that are allocated for an order may depend upon the size/amount/level/scope of the requested service. For example, the number of pods to be allocated may be determined based upon the number of users to be supported by the service, the duration of time for which the service is being requested, and the like. The allocated pods may then be customized for the particular requesting client for providing the requested service.

Cloud infrastructure system 802 may send a response or notification 844 to the requesting client to indicate when the requested service is now ready for use. In some instances, information (e.g., a link) may be sent to the client that enables the client to start using and availing the benefits of the requested services.

Cloud infrastructure system 802 may provide services to multiple clients. For each client, cloud infrastructure system 802 is responsible for managing information related to one or more subscription orders received from the client, maintaining client data related to the orders, and providing the requested services to the client. Cloud infrastructure system 802 may also collect usage statistics regarding a client's use of subscribed services. For example, statistics may be collected for the amount of storage used, the amount of data transferred, the number of users, and the amount of system up time and system down time, and the like. This usage information may be used to bill the client. Billing may be done, for example, on a monthly cycle.

Cloud infrastructure system 802 may provide services to multiple clients in parallel. Cloud infrastructure system 802 may store information for these clients, including possibly proprietary information. In certain aspects, cloud infrastructure system 802 comprises an identity management subsystem (IMS) 828 that is configured to manage client's information and provide the separation of the managed information such that information related to one client is not accessible by another client. IMS 828 may be configured to provide various security-related services such as identity services, such as information access management, authentication and authorization services, services for managing client identities and roles and related capabilities, and the like.

Figure 9:
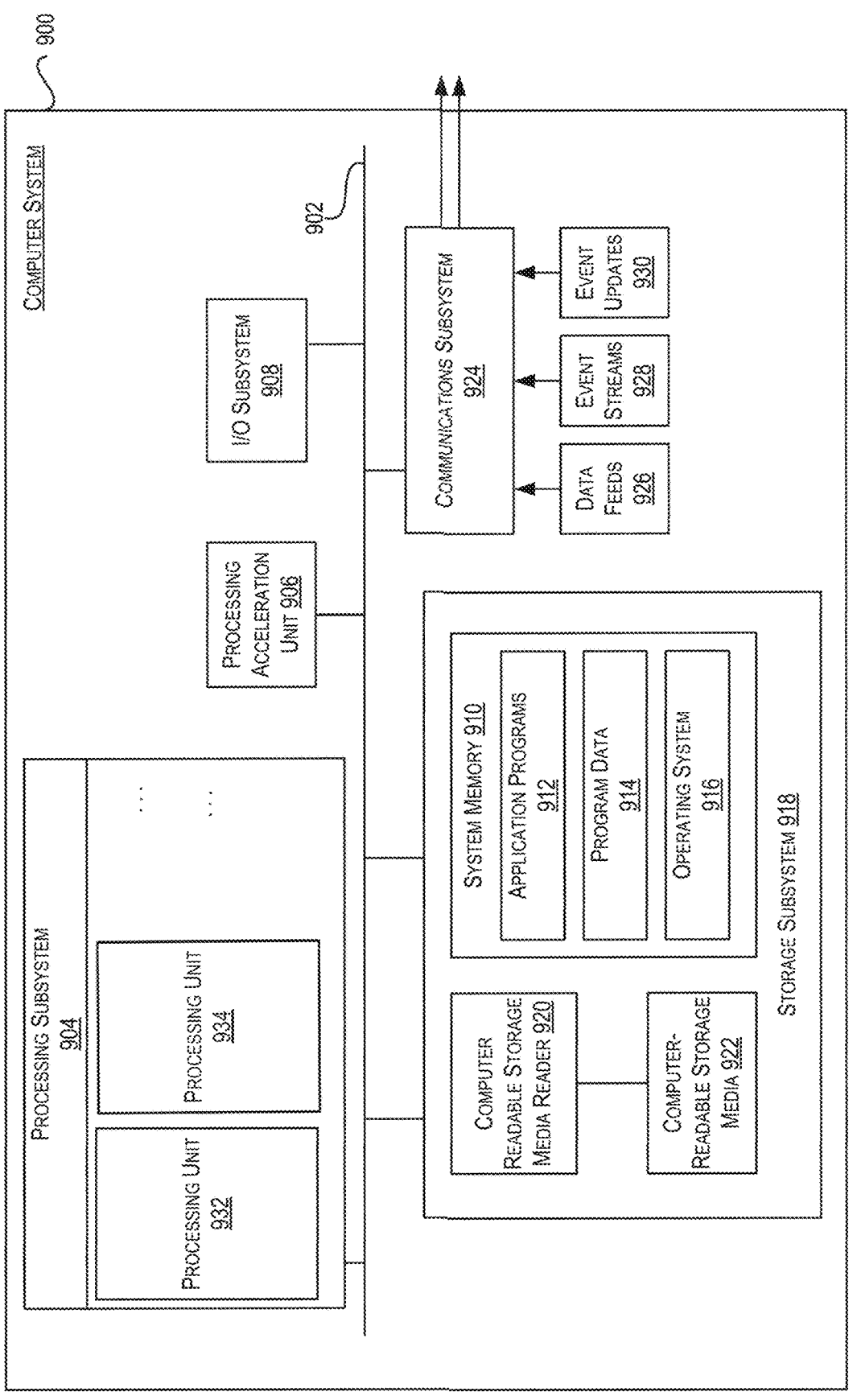
FIG. 9 illustrates an example computer system that may be used to implement certain aspects.

FIG. 9 illustrates an exemplary computer system 900 that may be used to implement certain aspects. For example, in some aspects, computer system 900 may be used to implement any of the system 100 for enriching log records with fields from other log records in structured format as shown in FIG. 1 and various servers and computer systems described above. As shown in FIG. 9, computer system 900 includes various subsystems including a processing subsystem 904 that communicates with a number of other subsystems via a bus subsystem 902. These other subsystems may include a processing acceleration unit 906, an I/O subsystem 908, a storage subsystem 918, and a communications subsystem 924. Storage subsystem 918 may include non-transitory computer-readable storage media including storage media 922 and a system memory 910.

Bus subsystem 902 provides a mechanism for letting the various components and subsystems of computer system 900 communicate with each other as intended. Although bus subsystem 902 is shown schematically as a single bus, alternative aspects of the bus subsystem may utilize multiple buses. Bus subsystem 902 may be any of several types of bus structures including a memory bus or memory controller, a peripheral bus, a local bus using any of a variety of bus architectures, and the like. For example, such architectures may include an Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, which can be implemented as a Mezzanine bus manufactured to the IEEE P1386.1 standard, and the like.

Processing subsystem 904 controls the operation of computer system 900 and may comprise one or more processors, application specific integrated circuits (ASICs), or field programmable gate arrays (FPGAs). The processors may include be single core or multicore processors. The processing resources of computer system 900 can be organized into one or more processing units 932, 934, etc. A processing unit may include one or more processors, one or more cores from the same or different processors, a combination of cores and processors, or other combinations of cores and processors. In some aspects, processing subsystem 904 can include one or more special purpose co-processors such as graphics processors, digital signal processors (DSPs), or the like. In some aspects, some or all of the processing units of processing subsystem 904 can be implemented using customized circuits, such as application specific integrated circuits (ASICs), or field programmable gate arrays (FPGAs).

In some aspects, the processing units in processing subsystem 904 can execute instructions stored in system memory 910 or on computer readable storage media 922. In various aspects, the processing units can execute a variety of programs or code instructions and can maintain multiple concurrently executing programs or processes. At any given time, some or all of the program code to be executed can be resident in system memory 910 and/or on computer-readable storage media 922 including potentially on one or more storage devices. Through suitable programming, processing subsystem 904 can provide various functionalities described above. In instances where computer system 900 is executing one or more virtual machines, one or more processing units may be allocated to each virtual machine.

In certain aspects, a processing acceleration unit 906 may optionally be provided for performing customized processing or for off-loading some of the processing performed by processing subsystem 904 so as to accelerate the overall processing performed by computer system 900.

I/O subsystem 908 may include devices and mechanisms for inputting information to computer system 900 and/or for outputting information from or via computer system 900. In general, use of the term input device is intended to include all possible types of devices and mechanisms for inputting information to computer system 900. User interface input devices may include, for example, a keyboard, pointing devices such as a mouse or trackball, a touchpad or touch screen incorporated into a display, a scroll wheel, a click wheel, a dial, a button, a switch, a keypad, audio input devices with voice command recognition systems, microphones, and other types of input devices. User interface input devices may also include motion sensing and/or gesture recognition devices such as the Microsoft Kinect® motion sensor that enables users to control and interact with an input device, the Microsoft Xbox® 360 game controller, devices that provide an interface for receiving input using gestures and spoken commands. User interface input devices may also include eye gesture recognition devices such as a blink detector that detects eye activity (e.g., "blinking" while taking pictures and/or making a menu selection) from users and transforms the eye gestures as inputs to an input device (e.g., Apple Vision Pro®, Ray-Ban® Meta Smart Glasses®, Google Glass®). Additionally, user interface input devices may include voice recognition sensing devices that enable users to interact with voice recognition systems (e.g., Siri® navigator) through voice commands.

Other examples of user interface input devices include, without limitation, three dimensional (3D) mice, joysticks or pointing sticks, gamepads and graphic tablets, and audio/visual devices such as speakers, digital cameras, digital camcorders, portable media players, webcams, image scanners, fingerprint scanners, barcode reader 3D scanners, 3D printers, laser rangefinders, and eye gaze tracking devices. Additionally, user interface input devices may include, for example, medical imaging input devices such as computed tomography, magnetic resonance imaging, position emission tomography, and medical ultrasonography devices. User interface input devices may also include, for example, audio input devices such as MIDI keyboards, digital musical instruments, and the like.

In general, use of the term output device is intended to include all possible types of devices and mechanisms for outputting information from computer system 900 to a user or other computer. User interface output devices may include a display subsystem, indicator lights, or non-visual displays such as audio output devices, etc. The display subsystem may be a cathode ray tube (CRT), a flat-panel device, such as that using a liquid crystal display (LCD) or plasma display, a projection device, a touch screen, and the like. For example, user interface output devices may include, without limitation, a variety of display devices that visually convey text, graphics, and audio/video information such as monitors, printers, speakers, headphones, automotive navigation systems, plotters, voice output devices, and modems.

Storage subsystem 918 provides a repository or data store for storing information and data that is used by computer system 900. Storage subsystem 918 provides a tangible non-transitory computer-readable storage medium for storing the basic programming and data constructs that provide the functionality of some aspects. Storage subsystem 918 may store software (e.g., programs, code modules, instructions) that when executed by processing subsystem 904 provides the functionality described above. The software may be executed by one or more processing units of processing subsystem 904. Storage subsystem 918 may also provide a repository for storing data used in accordance with the teachings of this disclosure.

Storage subsystem 918 may include one or more non-transitory memory devices, including volatile and non-volatile memory devices. As shown in FIG. 9, storage subsystem 918 includes a system memory 910 and a computer-readable storage media 922. System memory 910 may include a number of memories including a volatile main random access memory (RAM) for storage of instructions and data during program execution and a non-volatile read only memory (ROM) or flash memory in which fixed instructions are stored. In some implementations, a basic input/output system (BIOS), containing the basic routines that help to transfer information between elements within computer system 900, such as during start-up, may typically be stored in the ROM. The RAM typically contains data and/or program modules that are presently being operated and executed by processing subsystem 904. In some implementations, system memory 910 may include multiple different types of memory, such as static random access memory (SRAM), dynamic random access memory (DRAM), and the like.

By way of example, and not limitation, as depicted in FIG. 9, system memory 910 may load application programs 912 that are being executed, which may include various applications such as Web browsers, mid-tier applications, relational database management systems (RDBMS), etc., program data 914, and an operating system 916. By way of example, operating system 916 may include various versions of Microsoft Windows®, Apple Macintosh®, and/or Linux operating systems, a variety of commercially-available UNIX® or UNIX-like operating systems (including without limitation the variety of GNU/Linux operating systems, the Google Chrome® OS, and the like) and/or mobile operating systems such as iOS, Windows® Phone, Android® OS, BlackBerry® OS, Palm® OS operating systems, and others.

Computer-readable storage media 922 may store programming and data constructs that provide the functionality of some aspects. Computer-readable media 922 may provide storage of computer-readable instructions, data structures, program modules, and other data for computer system 900. Software (programs, code modules, instructions) that, when executed by processing subsystem 904 provides the functionality described above, may be stored in storage subsystem 918. By way of example, computer-readable storage media 922 may include non-volatile memory such as a hard disk drive, a magnetic disk drive, an optical disk drive such as a CD ROM, digital video disc (DVD), a Blu-Ray® disk, or other optical media. Computer-readable storage media 922 may include, but is not limited to, Zip® drives, flash memory cards, universal serial bus (USB) flash drives, secure digital (SD) cards, DVD disks, digital video tape, and the like. Computer-readable storage media 922 may also include, solid-state drives (SSD) based on non-volatile memory such as flash-memory based SSDs, enterprise flash drives, solid state ROM, and the like, SSDs based on volatile memory such as solid state RAM, dynamic RAM, static RAM, dynamic random access memory (DRAM)-based SSDs, magnetoresistive RAM (MRAM) SSDs, and hybrid SSDs that use a combination of DRAM and flash memory based SSDs.

In certain aspects, storage subsystem 918 may also include a computer-readable storage media reader 920 that can further be connected to computer-readable storage media 922. Reader 920 may receive and be configured to read data from a memory device such as a disk, a flash drive, etc.

In certain aspects, computer system 900 may support virtualization technologies, including but not limited to virtualization of processing and memory resources. For example, computer system 900 may provide support for executing one or more virtual machines. In certain aspects, computer system 900 may execute a program such as a hypervisor that facilitated the configuring and managing of the virtual machines. Each virtual machine may be allocated memory, compute (e.g., processors, cores), I/O, and networking resources. Each virtual machine generally runs independently of the other virtual machines. A virtual machine typically runs its own operating system, which may be the same as or different from the operating systems executed by other virtual machines executed by computer system 900. Accordingly, multiple operating systems may potentially be run concurrently by computer system 900.

Communications subsystem 924 provides an interface to other computer systems and networks. Communications subsystem 924 serves as an interface for receiving data from and transmitting data to other systems from computer system 900. For example, communications subsystem 924 may enable computer system 900 to establish a communication channel to one or more client devices via the Internet for receiving and sending information from and to the client devices. For example, the communication subsystem may be used to transmit a response to a user regarding the inquiry for a Chabot.

Communication subsystem 924 may support both wired and/or wireless communication protocols. For example, in certain aspects, communications subsystem 924 may include radio frequency (RF) transceiver components for accessing wireless voice and/or data networks (e.g., using cellular telephone technology, advanced data network technology, such as 3G, 4G or EDGE (enhanced data rates for global evolution), Wi-Fi (IEEE 802.XX family standards, or other mobile communication technologies, or any combination thereof), global positioning system (GPS) receiver components, and/or other components. In some aspects communications subsystem 924 can provide wired network connectivity (e.g., Ethernet) in addition to or instead of a wireless interface.

Communication subsystem 924 can receive and transmit data in various forms. For example, in some aspects, in addition to other forms, communications subsystem 924 may receive input communications in the form of structured and/or unstructured data feeds 926, event streams 928, event updates 930, and the like. For example, communications subsystem 924 may be configured to receive (or send) data feeds 926 in real-time from users of social media networks and/or other communication services such as Twitter® feeds, Facebook® updates, web feeds such as Rich Site Summary (RSS) feeds, and/or real-time updates from one or more third party information sources.

In certain aspects, communications subsystem 924 may be configured to receive data in the form of continuous data streams, which may include event streams 928 of real-time events and/or event updates 930, that may be continuous or unbounded in nature with no explicit end. Examples of applications that generate continuous data may include, for example, sensor data applications, financial tickers, network performance measuring tools (e.g., network monitoring and traffic management applications), clickstream analysis tools, automobile traffic monitoring, and the like.

Communications subsystem 924 may also be configured to communicate data from computer system 900 to other computer systems or networks. The data may be communicated in various different forms such as structured and/or unstructured data feeds 926, event streams 928, event updates 930, and the like to one or more databases that may be in communication with one or more streaming data source computers coupled to computer system 900.

Computer system 900 can be one of various types, including a handheld portable device (e.g., an iPhone® cellular phone, an iPad® computing tablet, a personal digital assistant (PDA)), a wearable device (e.g., a Google Glass® head mounted display), a personal computer, a workstation, a mainframe, a kiosk, a server rack, or any other data processing system. Due to the ever-changing nature of computers and networks, the description of computer system 900 depicted in FIG. 9 is intended only as a specific example. Many other configurations having more or fewer components than the system depicted in FIG. 9 are possible. Based on the disclosure and teachings provided herein, a person of ordinary skill in the art can appreciate other ways and/or methods to implement the various aspects.

Although specific aspects have been described, various modifications, alterations, alternative constructions, and equivalents are possible. Embodiments are not restricted to operation within certain specific data processing environments, but are free to operate within a plurality of data processing environments. Additionally, although certain aspects have been described using a particular series of transactions and steps, it should be apparent to those skilled in the art that this is not intended to be limiting. Although some flowcharts describe operations as a sequential process, many of the operations can be performed in parallel or concurrently. In addition, the order of the operations may be rearranged. A process may have additional steps not included in the figure. Various features and aspects of the above-described aspects may be used individually or jointly.

Further, while certain aspects have been described using a particular combination of hardware and software, it should be recognized that other combinations of hardware and software are also possible. Certain aspects may be implemented only in hardware, or only in software, or using combinations thereof. The various processes described herein can be implemented on the same processor or different processors in any combination.

Where devices, systems, components or modules are described as being configured to perform certain operations or functions, such configuration can be accomplished, for example, by designing electronic circuits to perform the operation, by programming programmable electronic circuits (such as microprocessors) to perform the operation such as by executing computer instructions or code, or processors or cores programmed to execute code or instructions stored on a non-transitory memory medium, or any combination thereof. Processes can communicate using a variety of techniques including but not limited to conventional techniques for inter-process communications, and different pairs of processes may use different techniques, or the same pair of processes may use different techniques at different times.

Specific details are given in this disclosure to provide a thorough understanding of the aspects. However, aspects may be practiced without these specific details. For example, well-known circuits, processes, algorithms, structures, and techniques have been shown without unnecessary detail in order to avoid obscuring the aspects. This description provides example aspects only, and is not intended to limit the scope, applicability, or configuration of other aspects. Rather, the preceding description of the aspects can provide those skilled in the art with an enabling description for implementing various aspects. Various changes may be made in the function and arrangement of elements.

The specification and drawings are, accordingly, to be regarded in an illustrative rather than a restrictive sense. It can, however, be evident that additions, subtractions, deletions, and other modifications and changes may be made thereunto without departing from the broader spirit and scope as set forth in the claims. Thus, although specific aspects have been described, these are not intended to be limiting. Various modifications and equivalents are within the scope of the following claims.

Although specific aspects have been described, various modifications, alterations, alternative constructions, and equivalents are possible. Embodiments are not restricted to operation within certain specific data processing environments but are free to operate within a plurality of data processing environments. Additionally, although certain aspects have been described using a particular series of transactions and steps, it should be apparent to those skilled in the art that this is not intended to be limiting. Although some flowcharts describe operations as a sequential process, many of the operations can be performed in parallel or concurrently. In addition, the order of the operations may be rearranged. A process may have additional steps not included in the figure. Various features and aspects of the above-described aspects may be used individually or jointly.

Further, while certain aspects have been described using a particular combination of hardware and software, it should be recognized that other combinations of hardware and software are also possible. Certain aspects may be implemented only in hardware, or only in software, or using combinations thereof. The various processes described herein can be implemented on the same processor or different processors in any combination.

Where devices, systems, components or modules are described as being configured to perform certain operations or functions, such configuration can be accomplished, for example, by designing electronic circuits to perform the operation, by programming programmable electronic circuits (such as microprocessors) to perform the operation such as by executing computer instructions or code, or processors or cores programmed to execute code or instructions stored on a non-transitory memory medium, or any combination thereof. Processes can communicate using a variety of techniques including but not limited to techniques for inter-process communications, and different pairs of processes may use different techniques, or the same pair of processes may use different techniques at different times.

Specific details are given in this disclosure to provide a thorough understanding of the aspects. However, aspects may be practiced without these specific details. For example, well-known circuits, processes, algorithms, structures, and techniques have been shown without unnecessary detail in order to avoid obscuring the aspects. This description provides example aspects only, and is not intended to limit the scope, applicability, or configuration of other aspects. Rather, the preceding description of the aspects can provide those skilled in the art with an enabling description for implementing various aspects. Various changes may be made in the function and arrangement of elements.

The specification and drawings are, accordingly, to be regarded in an illustrative rather than a restrictive sense. It can, however, be evident that additions, subtractions, deletions, and other modifications and changes may be made thereunto without departing from the broader spirit and scope as set forth in the claims. Thus, although specific aspects have been described, these are not intended to be limiting. Various modifications and equivalents are within the scope of the following claims.

What is claimed is:

1. A computer-implemented method, the method comprising:

querying at least one data source for one or more treatment plan templates, wherein the at least one data source is queried based on a medical condition of a patient;

receiving raw data related to the one or more treatment plan templates from the at least one data source in response to the querying, wherein the raw data includes text information;

parsing the raw data and identifying one or more tags from the parsed raw data;

extracting elements required for preparing treatment plan from the one or more tags using complex regular expression and a standard set of keywords;

constructing formatted data from the extracted elements in a machine-readable format, wherein the elements is arranged in a hierarchical structure within the formatted data;

generating structured data having one or more data frames based on the formatted data, wherein each data frame of the one or more data frames includes information related to a particular phase of a treatment schedule proposed in the one or more treatment plan templates;

providing the structured data to one or more devices associated with a medical provider for review, wherein the structured data is provided to the medical provider in a natural language format;

receiving an update in the structured data from the one or more devices associated with the medical provider, wherein the update is received based on a deviation in existing schedule provided in the one or more treatment plan templates; and generating one or more treatment plans based on incorporation of the update into the structured data, wherein the one or more treatment plans are generated in at least one of the machine-readable format and the natural language format.

2. The method of claim 1, wherein the formatted data is constructed using one or more headings present in the text information of the raw data.

3. The method of claim 1, wherein the formatted data is accessible by one or more applications pertaining to a health-care system.

4. The method of claim 1, wherein the raw data is received from the at least one data source using an Application Programming Interface (API).

5. The method of claim 1, wherein the raw data is received in form of one or more of an Extensible Markup Language (XML) format, a Hypertext Markup Language (HTML) format, and a Portable Document Format (PDF) format.

6. The method of claim 1, wherein the machine-readable format is a Java Script Object Notation (JSON) format.

7. The method of claim 1, wherein the structured data is provided to the one or more devices associated with the medical provider in a spreadsheet format.

8. The method of claim 1, wherein the one or more treatment plans are generated in XML format.

9. The method of claim 1, wherein the complex regular expression and the standard set of keywords are dynamically updated in real time.

10. The method of claim 1, wherein the one or more tags include a Unique Identification Number (UIN) or Universal Unique Identifier (UUID) that are generated programmatically.

11. The method of claim 1, wherein the medical condition of the patient is determined based on information obtained from a patient information database.

12. The method of claim 1, further comprising:

identifying one or more errors in the structured data based on the review of the medical provider;

updating the structured data based on the one or more errors; and generating the one or more treatment plans based on the updated structured data.

13. A system comprising:

one or more processors; and a memory coupled to the one or more processors, the memory storing a plurality of instructions executable by the one or more processors, the plurality of instructions that when executed by the one or more processors cause the one or more processors to perform a set of operations comprising:

querying at least one data source for one or more treatment plan templates, wherein the at least one data source is queried based on a medical condition of a patient;

receiving raw data related to the one or more treatment plan templates from the at least one data source in response to the querying, wherein the raw data includes text information;

parsing the raw data and identifying one or more tags from the parsed raw data;

extracting elements required for preparing treatment plan from the one or more tags using complex regular expression and a standard set of keywords;

constructing formatted data from the extracted elements in a machine-readable format, wherein the elements are arranged in a hierarchical structure within the formatted data;

generating structured data having one or more data frames based on the formatted data, wherein each data frame of the one or more data frames includes information related to a particular phase of a treatment schedule proposed in the one or more treatment plan templates;

providing the structured data to one or more devices associated with a medical provider for review, wherein the structured data is provided to the medical provider in a natural language format;

receiving an update in the structured data from the one or more devices associated with the medical provider, wherein the update is received based on a deviation in existing schedule provided in the one or more treatment plan templates; and generating one or more treatment plans based on incorporation of the update into the structured data, wherein the one or more treatment plans are generated in at least one of the machine-readable format and the natural language format.

14. The system of claim 13, wherein the raw data is received from the at least one data source using an Application Programming Interface (API).

15. The system of claim 13, wherein the raw data is received in form of one or more of an Extensible Markup Language (XML) format, a Hypertext Markup Language (HTML) format, and a Portable Document Format (PDF) format.

16. The system of claim 13, wherein the machine-readable format is a Java Script Object Notation (JSON) format.

17. The system of claim 13, wherein the structured data is provided to the one or more devices associated with the medical provider in a spreadsheet format.

18. The system of claim 13, wherein the one or more treatment plans are generated in XML format.

19. The system of claim 13, wherein the one or more tags include a Unique Identification Number (UIN) or Universal Unique Identifier (UUID) that are generated programmatically.

20. A non-transitory computer-readable medium storing a plurality of instructions executable by one or more processors that cause the one or more processors to perform operations comprising:

querying at least one data source for one or more treatment plan templates, wherein the at least one data source is queried based on a medical condition of a patient; receiving raw data related to the one or more treatment plan templates from the at least one data source in response to the querying, wherein the raw data includes text information;

parsing the raw data and identifying one or more tags from the parsed raw data;

extracting elements from the one or more tags using complex regular expression and a standard set of keywords;

constructing formatted data from the extracted elements in a machine-readable format, wherein the elements are arranged in a hierarchical structure within the formatted data;

generating structured data having one or more data frames based on the formatted data, wherein each data frame of the one or more data frames includes information related to a particular phase of a treatment schedule proposed in the one or more treatment plan templates;

providing the structured data to one or more devices associated with a medical provider for review, wherein the structured data is provided to the medical provider in a natural language format;

receiving an update in the structured data from the one or more devices associated with the medical provider, wherein the update is received based on a deviation in existing schedule provided in the one or more treatment plan templates; and generating one or more treatment plans based on incorporation of the update into the structured data, wherein the one or more treatment plans are generated in at least one of the machine-readable format and the natural language format.

* * * * *